US009074011B2

(12) United States Patent
Parsons

(10) Patent No.: US 9,074,011 B2
(45) Date of Patent: Jul. 7, 2015

(54) USE OF PTEN-LONG LEADER SEQUENCE FOR TRANSMEMBRANE DELIVERY OF MOLECULES

(75) Inventor: Ramon Parsons, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/579,025

(22) PCT Filed: Feb. 17, 2011

(86) PCT No.: PCT/US2011/025312
§ 371 (c)(1),
(2), (4) Date: Mar. 20, 2013

(87) PCT Pub. No.: WO2011/103339
PCT Pub. Date: Aug. 25, 2011

(65) Prior Publication Data
US 2013/0171235 A1     Jul. 4, 2013

Related U.S. Application Data

(60) Provisional application No. 61/338,377, filed on Feb. 17, 2010.

(51) Int. Cl.
| | | |
|---|---|---|
| *A61K 38/00* | (2006.01) | |
| *C07K 14/47* | (2006.01) | |
| *A61K 47/48* | (2006.01) | |
| *C12N 9/16* | (2006.01) | |

(52) U.S. Cl.
CPC ............... *C07K 14/47* (2013.01); *A61K 38/00* (2013.01); *A61K 47/48246* (2013.01); *A61K 47/48315* (2013.01); *C12N 9/16* (2013.01); *C12Y 301/03048* (2013.01)

(58) Field of Classification Search
None
See application file for complete search history.

(56) References Cited

U.S. PATENT DOCUMENTS

| 6,482,795 | B1 * | 11/2002 | Steck et al. .................. 514/19.2 |
|---|---|---|---|
| 2003/0139324 | A1 | 7/2003 | Steck et al. |
| 2007/0054333 | A1 | 3/2007 | Steck et al. |
| 2012/0039861 | A1 | 2/2012 | Parsons |

FOREIGN PATENT DOCUMENTS

WO    WO 2010/096173 A2    8/2010

OTHER PUBLICATIONS

Notification of Transmittal of the International Search Report and the Written Opinion of the International Searching Authority, or the Declaration, including an International Search Report and Written Opinion of the International Searching Authority, mailed Jun. 15, 2011 in connection with PCT International Application No. PCT/US2011/025312, filed Feb. 17, 2011.
Notification Concerning Transmittal of International Preliminary Report on Patentability (Chapter I of the Patent Cooperation Treaty), including an International Preliminary Report on Patentability and Written Opinion of the International Searching Authority, mailed Aug. 30, 2012 by the International Bureau of WIPO in connection with PCT International Application No. PCT/US2011/025312, filed Feb. 17, 2011.
Jul. 3, 2013 Office Action issued in connection with U.S. Appl. No. 13/201,969.
Jan. 3, 2014 Response to Jul. 3, 2013 Office Action in connection with U.S. Appl. No. 13/201,969.
Apr. 30, 2014 Office Action issued in connection with U.S. Appl. No. 13/201,969.
Apr. 11, 2013 Office Action issued in connection with Chinese Patent Application No. 2010800163333 (including English Language translation).
Oct. 25, 2013 Response to Apr. 11, 2013 Office Action issued in connection with Chinese Patent Application No. 2010800163333 (including English translation of coverpage).
Nov. 26, 2013 Office Action issued in connection with Chinese Patent Application No. 2010800163333 (including English Language translation).
Apr. 11, 2014 Response to Nov. 26, 2013 Office Action issued in connection with Chinese Patent Application No. 2010800163333 (including English translation of coverpage).
Jun. 3, 2014 Office Action issued in connection with Chinese Patent Application No. 2010800163333 (including English translation of coverpage).
Feb. 12, 2013 Office Action issued in connection with European Patent Application No. 10744058.8.
Aug. 22, 2013 Response to Feb. 12, 2013 Office Action issued in connection with European Patent Application No. 10744058.8.
Sep. 30, 2013 Office Action issued in connection with European Patent Application No. 10744058.8.
Apr. 10, 2014 Response to Sep. 30, 2013 Office Action issued in connection with European Patent Application No. 10744058.8.
May 22, 2014 Office Action issued in connection with European Patent Application No. 10744058.8.
Jul. 2, 2013 Office Action in connection with Chinese Application No. 201180018210.8 (with English Language translation).
Jan. 17, 2014 Response to the Jul. 2, 2013 Office Action in connection with Chinese Application No. 201180018210.8 (including English translation of coverpage).
Apr. 11, 2014 Second Office Action in connection with Chinese Application No. 201180018210.8 (including English Language translation).

(Continued)

*Primary Examiner* — Sheela J Huff
(74) *Attorney, Agent, or Firm* — John P. White; Cooper & Dunham LLP

(57) ABSTRACT

A composition for delivering cargo molecules across biological membranes is provided comprising (i) a peptide comprising consecutive amino acid residues having the sequence set forth in SEQ ID NO 1 for the transport of a cargo molecule across a biological membrane and (ii) the cargo molecule, wherein the cargo molecule is not a peptide comprising amino acid residues having the sequence set forth in SEQ ID NO 4. Methods of delivering cargo molecules across biological membranes are also provided. Methods of treating a tumor, cancer, a metabolic disorder, and a cardiovascular disorder are also provided.

7 Claims, 32 Drawing Sheets

(56) References Cited

OTHER PUBLICATIONS

Jun. 26, 2014 Response to the Apr. 11, 2014 Second Office Action in connection with Chinese Application No. 201180018210.8 (including English translation of coverpage).
Fine, Barry Michael "Analysis of PTEN function and regulation" Columbia University, Dissertation, Sep. 2008, AAT 3305221.
Georgescu et al. Proc. Natl. Acad. Sci. U.S.A. (1999) vol. 96, No. 18, p. 10182-10187.
Wu et al. "Interaction of the tumor suppressor PTEN/MMAC with a PDZ domain of MAG13, a novel membrane-associated guanylate kinase." The Journal of Biological Chemistry Jul. 14, 2000, vol. 275, No. 28, Jul. 14, 2000, pp. 21477-21485, ISSN: 0021-9258.
Oct. 30, 2014 Response to Apr. 30, 2014 Office Action issued in connection with U.S. Appl. No. 13/201,969.
Dec. 15, 2014 Notice of Allowance and Allowability including Notice of Fees in connection with U.S. Appl. No. 13/201,969.
Dec. 1, 2014 response to May 22, 2014 Office Action issued in connection with European Patent Application No. 10744058.8.
Jan. 22, 2015 supplemental response to May 22, 2014 Office Action issued in connection with European Patent Application No. 10744058.8.
Fine, Barry Michael "Analysis of PTEN function and regulation" Columbia University, Dissertation, 2008, AAT 3305221.

\* cited by examiner

Fig. 3

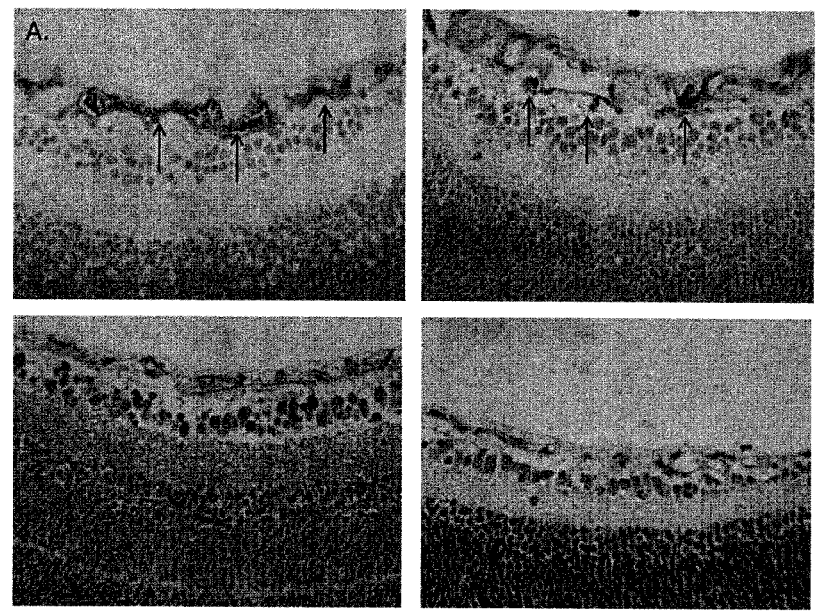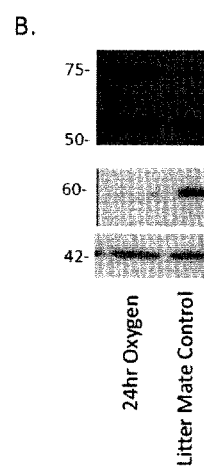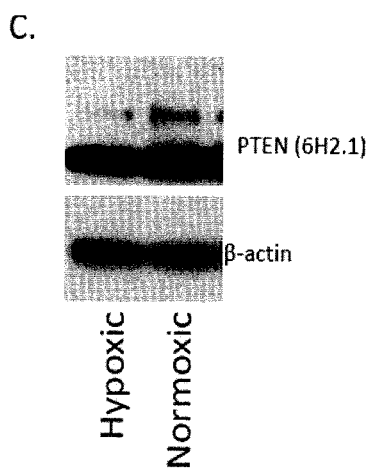
Fig. 11

MCF10a Treated with
Purified Proteins for 24hrs as indicated

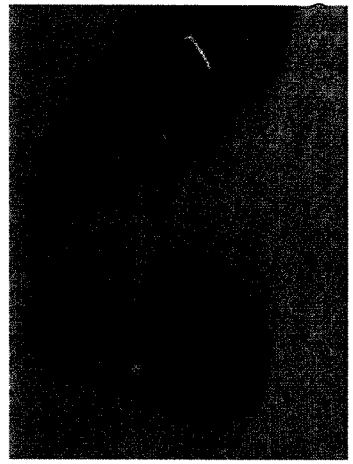
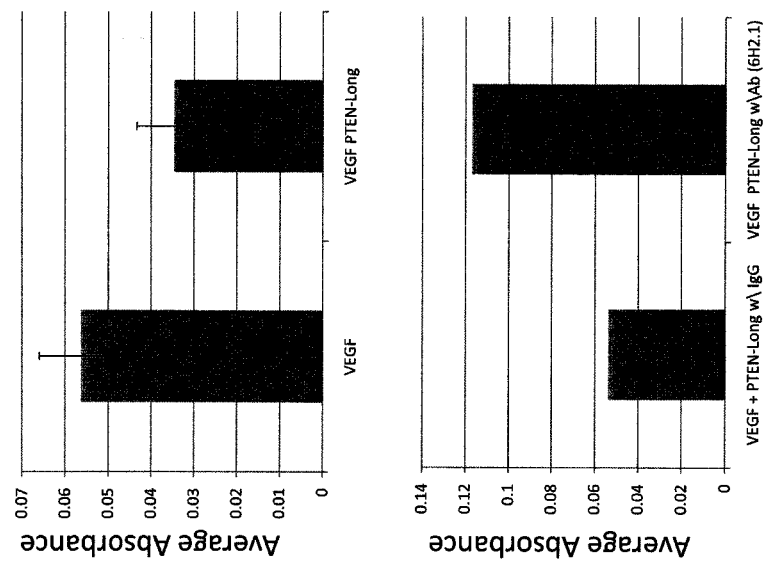
Fig. 26

```
M E R G G E A A A A A A A A A A A P G R G S E S P V T I S R A G
N A G E L V S P L L L P P T R R R R R R H I Q G P G P V L N L P S
A A A A P P V A R A P E A A G G G S R S E D Y S S S P H S A A A
A A R P L A A E E K Q A Q S L Q P S S S R R S S H Y P A A V Q S Q
A A A E R G A S A T A K S R A I S I L Q K K P R H Q Q L L P S L S
S F F F S H R L P D M T A I I K E I V S R N K R R Y Q E D G F D L
D L T Y I Y P N I I A M G F P A E R L E G V Y R N N I D D V V R F
L D S K H K N H Y K I Y N L C A E R H Y D T A K F N C R V A Q Y
P F E D H N P P Q L E L I K P F C E D L D Q W L S E D D N H V A A
I H C K A G K G R T G V M I C A Y L L H R G K F L K A Q E A L D
F Y G E V R T R D K K G V T I P S Q R R Y V Y Y Y S Y L L K N H
L D Y R P V A L L F H K M M F E T I P M F S G G T C N P Q F V V
C Q L K V K I Y S S N S G P T R R E D K F M Y F E F P Q P L P V C
G D I K V E F F H K Q N K M L K K D K M F H F W V N T F F I P G
P E E T S E K V E N G S L C D Q E I D S I C S I E R A D N D K E Y L
V L T L T K N D L D K A N K D K A N R Y F S P N F K V K L Y F T
K T V E E P S N P E A S S S T S V T P D V S D N E P D H Y R Y S D
T T D S D P E N E P F D E D Q H T Q I T K V (SEQ ID NO:5)
```

Figure 27

MSESPVTISRAGNAGELVSPLLLPPT<u>RRRRRR</u>HIQGPGPVLNLPSAAAAPPVARAP
EAAGGGSRSEDYSSSPHSAAAAARPLAAEEKQAQSLQPSSSRRSSHYPAAVQSQA
AAERGASATAKSRAISILQKKPRHQQLLPSLSSFFFSHRLP<u>D</u>MTAIIKEIVSRNKRR
YQEDGFDLDLTYIYPNIIAMGFPAERLEGVYRNNIDDVVRFLDSKHKNHYKIYNL
CAERHYDTAKFNCRVAQYPFEDHNPPQLELIKPFCEDLDQWLSEDDNHVAAIHC
KAGKGRTGVMICAYLLHRGKFLKAQEALDFYGEVRTRDKKGVTIPSQRRYVYY
YSYLLKNHLDYRPVALLFHKMMFETIPMFSGGTCNPQFVVCQLKVKIYSSNSGPT
RREDKFMYFEFPQPLPVCGDIKVEFFHKQNKMLKKDKMFHFWVNTFFIPGPEETS
EKVENGSLCDQEIDSICSIERADNDKEYLVLTLTKNDLDKANKDKANRYFSPNFK
VKLYFTKTVEEPSNPEASSSTSVTPDVSDNEPDHYRYSDTTDSDPENEPFDEDQHT
QITKV (SEQ ID NO:6)

*KGNSADIQHSGGRSSLEGPRFEGKPIPNPLLGLDSTRTGHHHHHH* (SEQ ID NO:7)

Figure 28

MSESPVTISRAGNAGELVSPLLLPPTRRRRRRHIQGPGPVLNLPSAAAAPPVARAPEAAG
GGSRSEDYSSSPHSAAAAARPLAAEEKQAQSLQPSSSRRSSHYPAAVQSQAAAERGASA
TAKSRAISILQKKPRHQQLLPSLSSFFFSHRLPDMEEPQSDPSVEPPLSQETFSDLWKLLPE
NNVLSPLPSQAMDDLMLSPDDIEQWFTEDPGPDEAPRMPEAAPPVAPAPAAPTPAAPAP
APSWPLSSSVPSQKTYQGSYGFRLGFLHSGTAKSVTCTYSPALNKMFCQLAKTCPVQLW
VDSTPPPGTRVRAMAIYKQSQHMTEVVRRCPHHERCSDSDGLAPPQHLIRVEGNLRVEY
LDDRNTFRHSVVVPYEPPEVGSDCTTIHYNYMCNSSCMGGMNRRPILTIITLEDSSGNLL
GRNSFEVRVCACPGRDRRTEEENLRKKGEPHHELPPGSTKRALPNNTSSSPQPKKKPLDG
EYFTLQIRGRERFEMFRELNEALELKDAQAGKEPGGSRAHSSHLKSKKGQSTSRHKKLM
FKTEGPDSD (SEQ ID NO:8)

*KGNSADIQHSGGRSSLEGPRFEGKPIPNPLLGLDSTRTGHHHHHH* (SEQ ID NO:7)

Figure 30

SEQUENCE LISTING

```
<160> NUMBER OF SEQ ID NOS: 17

<210> SEQ ID NO 1
<211> LENGTH: 173
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: Signal Sequence of PTEN

<400> SEQUENCE: 1
```

```
Leu Glu Arg Gly Gly Glu Ala Ala Ala Ala Ala Ala Ala Ala Ala
1               5                   10                  15

Ala Pro Gly Arg Gly Ser Glu Ser Pro Val Thr Ile Ser Arg Ala Gly
            20                  25                  30

Asn Ala Gly Glu Leu Val Ser Pro Leu Leu Leu Pro Pro Thr Arg Arg
        35                  40                  45

Arg Arg Arg Arg His Ile Gln Gly Pro Gly Pro Val Leu Asn Leu Pro
    50                  55                  60

Ser Ala Ala Ala Ala Pro Val Ala Arg Ala Pro Glu Ala Ala Gly
65                  70                  75                  80

Gly Gly Ser Arg Ser Glu Asp Tyr Ser Ser Pro His Ser Ala Ala
                85                  90                  95

Ala Ala Ala Arg Pro Leu Ala Ala Glu Glu Lys Gln Ala Gln Ser Leu
            100                 105                 110

Gln Pro Ser Ser Ser Arg Arg Ser Ser His Tyr Pro Ala Ala Val Gln
            115                 120                 125

Ser Gln Ala Ala Ala Glu Arg Gly Ala Ser Ala Thr Ala Lys Ser Arg
        130                 135                 140

Ala Ile Ser Ile Leu Gln Lys Lys Pro Arg His Gln Gln Leu Leu Pro
145                 150                 155                 160

Ser Leu Ser Ser Phe Phe Phe Ser His Arg Leu Pro Asp
                165                 170
```

<210> SEQ ID NO 2
<211> LENGTH: 173
<212> TYPE: PRT
<213> ORGANISM: Homo sapiens

<400> SEQUENCE: 2

```
Met Glu Arg Gly Gly Glu Ala Ala Ala Ala Ala Ala Ala Ala Ala Ala
1               5                   10                  15

Ala Pro Gly Arg Gly Ser Glu Ser Pro Val Thr Ile Ser Arg Ala Gly
            20                  25                  30

Asn Ala Gly Glu Leu Val Ser Pro Leu Leu Leu Pro Pro Thr Arg Arg
        35                  40                  45

Arg Arg Arg Arg His Ile Gln Gly Pro Gly Pro Val Leu Asn Leu Pro
    50                  55                  60

Ser Ala Ala Ala Ala Pro Val Ala Arg Ala Pro Glu Ala Ala Gly
65                  70                  75                  80

Gly Gly Ser Arg Ser Glu Asp Tyr Ser Ser Pro His Ser Ala Ala
                85                  90                  95

Ala Ala Ala Arg Pro Leu Ala Ala Glu Glu Lys Gln Ala Gln Ser Leu
            100                 105                 110

Gln Pro Ser Ser Ser Arg Arg Ser Ser His Tyr Pro Ala Ala Val Gln
            115                 120                 125

Ser Gln Ala Ala Ala Glu Arg Gly Ala Ser Ala Thr Ala Lys Ser Arg
        130                 135                 140

Ala Ile Ser Ile Leu Gln Lys Lys Pro Arg His Gln Gln Leu Leu Pro
145                 150                 155                 160

Ser Leu Ser Ser Phe Phe Phe Ser His Arg Leu Pro Asp
                165                 170
```

<210> SEQ ID NO 3
<211> LENGTH: 21
<212> TYPE: PRT
<213> ORGANISM: Homo sapiens

<400> SEQUENCE: 3

Pro Arg His Gln Gln Leu Leu Pro Ser Leu Ser Ser Phe Phe Ser
1               5                   10                  15

His Arg Leu Pro Asp
            20

<210> SEQ ID NO 4
<211> LENGTH: 403
<212> TYPE: PRT
<213> ORGANISM: Homo sapiens

<400> SEQUENCE: 4

Met Thr Ala Ile Ile Lys Glu Ile Val Ser Arg Asn Lys Arg Tyr
1               5                   10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
            130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
            290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

```
Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Thr Gln Ile
385                 390                 395                 400

Thr Lys Val

<210> SEQ ID NO 5
<211> LENGTH: 576
<212> TYPE: PRT
<213> ORGANISM: Homo sapiens

<400> SEQUENCE: 5

Met Glu Arg Gly Gly Glu Ala Ala Ala Ala Ala Ala Ala Ala Ala Ala
1               5                   10                  15

Ala Pro Gly Arg Gly Ser Glu Ser Pro Val Thr Ile Ser Arg Ala Gly
                20                  25                  30

Asn Ala Gly Glu Leu Val Ser Pro Leu Leu Leu Pro Pro Thr Arg Arg
            35                  40                  45

Arg Arg Arg Arg His Ile Gln Gly Pro Gly Pro Val Leu Asn Leu Pro
50                  55                  60

Ser Ala Ala Ala Ala Pro Pro Val Ala Arg Ala Pro Glu Ala Ala Gly
65                  70                  75                  80

Gly Gly Ser Arg Ser Glu Asp Tyr Ser Ser Ser Pro His Ser Ala Ala
                85                  90                  95

Ala Ala Ala Arg Pro Leu Ala Ala Glu Glu Lys Gln Ala Gln Ser Leu
            100                 105                 110

Gln Pro Ser Ser Ser Arg Arg Ser Ser His Tyr Pro Ala Ala Val Gln
        115                 120                 125

Ser Gln Ala Ala Ala Glu Arg Gly Ala Ser Ala Thr Ala Lys Ser Arg
130                 135                 140

Ala Ile Ser Ile Leu Gln Lys Lys Pro Arg His Gln Gln Leu Leu Pro
145                 150                 155                 160

Ser Leu Ser Ser Phe Phe Phe Ser His Arg Leu Pro Asp Met Thr Ala
                165                 170                 175

Ile Ile Lys Glu Ile Val Ser Arg Asn Lys Arg Arg Tyr Gln Glu Asp
            180                 185                 190

Gly Phe Asp Leu Asp Leu Thr Tyr Ile Tyr Pro Asn Ile Ile Ala Met
        195                 200                 205

Gly Phe Pro Ala Glu Arg Leu Glu Gly Val Tyr Arg Asn Asn Ile Asp
    210                 215                 220

Asp Val Arg Phe Leu Asp Ser Lys His Lys Asn His Tyr Lys Ile
225                 230                 235                 240

Tyr Asn Leu Cys Ala Glu Arg His Tyr Asp Thr Ala Lys Phe Asn Cys
                245                 250                 255

Arg Val Ala Gln Tyr Pro Phe Glu Asp His Asn Pro Pro Gln Leu Glu
            260                 265                 270

Leu Ile Lys Pro Phe Cys Glu Asp Leu Asp Gln Trp Leu Ser Glu Asp
        275                 280                 285

Asp Asn His Val Ala Ala Ile His Cys Lys Ala Gly Lys Gly Arg Thr
    290                 295                 300
```

```
Gly Val Met Ile Cys Ala Tyr Leu Leu His Arg Gly Lys Phe Leu Lys
305                 310                 315                 320

Ala Gln Glu Ala Leu Asp Phe Tyr Gly Glu Val Arg Thr Arg Asp Lys
                325                 330                 335

Lys Gly Val Thr Ile Pro Ser Gln Arg Arg Tyr Val Tyr Tyr Tyr Ser
            340                 345                 350

Tyr Leu Leu Lys Asn His Leu Asp Tyr Arg Pro Val Ala Leu Leu Phe
                355                 360                 365

His Lys Met Met Phe Glu Thr Ile Pro Met Phe Ser Gly Gly Thr Cys
370                 375                 380

Asn Pro Gln Phe Val Val Cys Gln Leu Lys Val Lys Ile Tyr Ser Ser
385                 390                 395                 400

Asn Ser Gly Pro Thr Arg Arg Glu Asp Lys Phe Met Tyr Phe Glu Phe
                405                 410                 415

Pro Gln Pro Leu Pro Val Cys Gly Asp Ile Lys Val Glu Phe Phe His
                420                 425                 430

Lys Gln Asn Lys Met Leu Lys Lys Asp Lys Met Phe His Phe Trp Val
                435                 440                 445

Asn Thr Phe Phe Ile Pro Gly Pro Glu Thr Ser Glu Lys Val Glu
                450                 455                 460

Asn Gly Ser Leu Cys Asp Gln Glu Ile Asp Ser Ile Cys Ser Ile Glu
465                 470                 475                 480

Arg Ala Asp Asn Asp Lys Glu Tyr Leu Val Leu Thr Leu Thr Lys Asn
                485                 490                 495

Asp Leu Asp Lys Ala Asn Lys Asp Lys Ala Asn Arg Tyr Phe Ser Pro
                500                 505                 510

Asn Phe Lys Val Lys Leu Tyr Phe Thr Lys Thr Val Glu Glu Pro Ser
                515                 520                 525

Asn Pro Glu Ala Ser Ser Thr Ser Val Thr Pro Asp Val Ser Asp
                530                 535                 540

Asn Glu Pro Asp His Tyr Arg Tyr Ser Asp Thr Thr Asp Ser Asp Pro
545                 550                 555                 560

Glu Asn Glu Pro Phe Asp Glu Asp Gln His Thr Gln Ile Thr Lys Val
                565                 570                 575

<210> SEQ ID NO 6
<211> LENGTH: 556
<212> TYPE: PRT
<213> ORGANISM: Homo sapiens

<400> SEQUENCE: 6

Met Ser Glu Ser Pro Val Thr Ile Ser Arg Ala Gly Asn Ala Gly Glu
1               5                   10                  15

Leu Val Ser Pro Leu Leu Leu Pro Pro Thr Arg Arg Arg Arg Arg Arg
                20                  25                  30

His Ile Gln Gly Pro Gly Pro Val Leu Asn Leu Pro Ser Ala Ala Ala
                35                  40                  45

Ala Pro Pro Val Ala Arg Ala Pro Glu Ala Gly Gly Gly Ser Arg
            50                  55                  60

Ser Glu Asp Tyr Ser Ser Pro His Ser Ala Ala Ala Ala Arg
65                  70                  75                  80

Pro Leu Ala Ala Glu Glu Lys Gln Ala Gln Ser Leu Gln Pro Ser Ser
                85                  90                  95

Ser Arg Arg Ser Ser His Tyr Pro Ala Ala Val Gln Ser Gln Ala Ala
```

```
                100                 105                 110
Ala Glu Arg Gly Ala Ser Ala Thr Ala Lys Ser Arg Ala Ile Ser Ile
            115                 120                 125

Leu Gln Lys Lys Pro Arg His Gln Leu Leu Pro Ser Leu Ser Ser
        130                 135                 140

Phe Phe Phe Ser His Arg Leu Pro Asp Met Thr Ala Ile Ile Lys Glu
145                 150                 155                 160

Ile Val Ser Arg Asn Lys Arg Arg Tyr Gln Glu Asp Gly Phe Asp Leu
                165                 170                 175

Asp Leu Thr Tyr Ile Tyr Pro Asn Ile Ile Ala Met Gly Phe Pro Ala
            180                 185                 190

Glu Arg Leu Glu Gly Val Tyr Arg Asn Asn Ile Asp Asp Val Val Arg
        195                 200                 205

Phe Leu Asp Ser Lys His Lys Asn His Tyr Lys Ile Tyr Asn Leu Cys
210                 215                 220

Ala Glu Arg His Tyr Asp Thr Ala Lys Phe Asn Cys Arg Val Ala Gln
225                 230                 235                 240

Tyr Pro Phe Glu Asp His Asn Pro Pro Gln Leu Glu Leu Ile Lys Pro
                245                 250                 255

Phe Cys Glu Asp Leu Asp Gln Trp Leu Ser Glu Asp Asp Asn His Val
            260                 265                 270

Ala Ala Ile His Cys Lys Ala Gly Lys Gly Arg Thr Gly Val Met Ile
        275                 280                 285

Cys Ala Tyr Leu Leu His Arg Gly Lys Phe Leu Lys Ala Gln Glu Ala
290                 295                 300

Leu Asp Phe Tyr Gly Glu Val Arg Thr Arg Asp Lys Lys Gly Val Thr
305                 310                 315                 320

Ile Pro Ser Gln Arg Arg Tyr Val Tyr Tyr Ser Tyr Leu Leu Lys
                325                 330                 335

Asn His Leu Asp Tyr Arg Pro Val Ala Leu Leu Phe His Lys Met Met
            340                 345                 350

Phe Glu Thr Ile Pro Met Phe Ser Gly Gly Thr Cys Asn Pro Gln Phe
        355                 360                 365

Val Val Cys Gln Leu Lys Val Lys Ile Tyr Ser Ser Asn Ser Gly Pro
370                 375                 380

Thr Arg Arg Glu Asp Lys Phe Met Tyr Phe Glu Phe Pro Gln Pro Leu
385                 390                 395                 400

Pro Val Cys Gly Asp Ile Lys Val Glu Phe Phe His Lys Gln Asn Lys
                405                 410                 415

Met Leu Lys Lys Asp Lys Met Phe His Phe Trp Val Asn Thr Phe Phe
            420                 425                 430

Ile Pro Gly Pro Glu Glu Thr Ser Glu Lys Val Glu Asn Gly Ser Leu
        435                 440                 445

Cys Asp Gln Glu Ile Asp Ser Ile Cys Ser Ile Glu Arg Ala Asp Asn
450                 455                 460

Asp Lys Glu Tyr Leu Val Leu Thr Leu Thr Lys Asn Asp Leu Asp Lys
465                 470                 475                 480

Ala Asn Lys Asp Lys Ala Asn Arg Tyr Phe Ser Pro Asn Phe Lys Val
                485                 490                 495

Lys Leu Tyr Phe Thr Lys Thr Val Glu Glu Pro Ser Asn Pro Glu Ala
            500                 505                 510

Ser Ser Ser Thr Ser Val Thr Pro Asp Val Ser Asp Asn Glu Pro Asp
        515                 520                 525
```

```
His Tyr Arg Tyr Ser Asp Thr Thr Asp Ser Asp Pro Glu Asn Glu Pro
            530                 535                 540

Phe Asp Glu Asp Gln His Thr Gln Ile Thr Lys Val
545                 550                 555

<210> SEQ ID NO 7
<211> LENGTH: 45
<212> TYPE: PRT
<213> ORGANISM: Artificial
<220> FEATURE:
<223> OTHER INFORMATION: v5-His epitope tag

<400> SEQUENCE: 7

Lys Gly Asn Ser Ala Asp Ile Gln His Ser Gly Gly Arg Ser Ser Leu
1               5                   10                  15

Glu Gly Pro Arg Phe Glu Gly Lys Pro Ile Pro Asn Pro Leu Leu Gly
            20                  25                  30

Leu Asp Ser Thr Arg Thr Gly His His His His His His
        35                  40                  45

<210> SEQ ID NO 8
<211> LENGTH: 546
<212> TYPE: PRT
<213> ORGANISM: Artificial
<220> FEATURE:
<223> OTHER INFORMATION: PTEN-long-p53 fusion protein

<400> SEQUENCE: 8

Met Ser Glu Ser Pro Val Thr Ile Ser Arg Ala Gly Asn Ala Gly Glu
1               5                   10                  15

Leu Val Ser Pro Leu Leu Leu Pro Pro Thr Arg Arg Arg Arg Arg Arg
            20                  25                  30

His Ile Gln Gly Pro Gly Pro Val Leu Asn Leu Pro Ser Ala Ala Ala
        35                  40                  45

Ala Pro Pro Val Ala Arg Ala Pro Glu Ala Ala Gly Gly Gly Ser Arg
    50                  55                  60

Ser Glu Asp Tyr Ser Ser Pro His Ser Ala Ala Ala Ala Ala Ala Arg
65                  70                  75                  80

Pro Leu Ala Ala Glu Glu Lys Gln Ala Gln Ser Leu Gln Pro Ser Ser
                85                  90                  95

Ser Arg Arg Ser Ser His Tyr Pro Ala Ala Val Gln Ser Gln Ala Ala
            100                 105                 110

Ala Glu Arg Gly Ala Ser Ala Thr Ala Lys Ser Arg Ala Ile Ser Ile
        115                 120                 125

Leu Gln Lys Lys Pro Arg His Gln Gln Leu Leu Pro Ser Leu Ser Ser
    130                 135                 140

Phe Phe Phe Ser His Arg Leu Pro Asp Met Glu Glu Pro Gln Ser Asp
145                 150                 155                 160

Pro Ser Val Glu Pro Leu Ser Gln Glu Thr Phe Ser Asp Leu Trp
                165                 170                 175

Lys Leu Leu Pro Glu Asn Asn Val Leu Ser Pro Leu Pro Ser Gln Ala
            180                 185                 190

Met Asp Asp Leu Met Leu Ser Pro Asp Ile Glu Gln Trp Phe Thr
        195                 200                 205

Glu Asp Pro Gly Pro Asp Glu Ala Pro Arg Met Pro Glu Ala Ala Pro
    210                 215                 220

Pro Val Ala Pro Ala Pro Ala Ala Pro Thr Pro Ala Ala Pro Ala Pro
```

```
                225                 230                 235                 240
Ala Pro Ser Trp Pro Leu Ser Ser Val Pro Ser Gln Lys Thr Tyr
                245                 250                 255

Gln Gly Ser Tyr Gly Phe Arg Leu Gly Phe Leu His Ser Gly Thr Ala
                260                 265                 270

Lys Ser Val Thr Cys Thr Tyr Ser Pro Ala Leu Asn Lys Met Phe Cys
                275                 280                 285

Gln Leu Ala Lys Thr Cys Pro Val Gln Leu Trp Val Asp Ser Thr Pro
                290                 295                 300

Pro Pro Gly Thr Arg Val Arg Ala Met Ala Ile Tyr Lys Gln Ser Gln
305                 310                 315                 320

His Met Thr Glu Val Val Arg Arg Cys Pro His His Glu Arg Cys Ser
                325                 330                 335

Asp Ser Asp Gly Leu Ala Pro Pro Gln His Leu Ile Arg Val Glu Gly
                340                 345                 350

Asn Leu Arg Val Glu Tyr Leu Asp Asp Arg Asn Thr Phe Arg His Ser
                355                 360                 365

Val Val Val Pro Tyr Glu Pro Pro Glu Val Gly Ser Asp Cys Thr Thr
370                 375                 380

Ile His Tyr Asn Tyr Met Cys Asn Ser Ser Cys Met Gly Gly Met Asn
385                 390                 395                 400

Arg Arg Pro Ile Leu Thr Ile Ile Thr Leu Glu Asp Ser Ser Gly Asn
                405                 410                 415

Leu Leu Gly Arg Asn Ser Phe Glu Val Arg Val Cys Ala Cys Pro Gly
                420                 425                 430

Arg Asp Arg Arg Thr Glu Glu Glu Asn Leu Arg Lys Lys Gly Glu Pro
                435                 440                 445

His His Glu Leu Pro Pro Gly Ser Thr Lys Arg Ala Leu Pro Asn Asn
                450                 455                 460

Thr Ser Ser Ser Pro Gln Pro Lys Lys Lys Pro Leu Asp Gly Glu Tyr
465                 470                 475                 480

Phe Thr Leu Gln Ile Arg Gly Arg Glu Arg Phe Glu Met Phe Arg Glu
                485                 490                 495

Leu Asn Glu Ala Leu Glu Leu Lys Asp Ala Gln Ala Gly Lys Glu Pro
                500                 505                 510

Gly Gly Ser Arg Ala His Ser Ser His Leu Lys Ser Lys Lys Gly Gln
                515                 520                 525

Ser Thr Ser Arg His Lys Lys Leu Met Phe Lys Thr Glu Gly Pro Asp
530                 535                 540

Ser Asp
545

<210> SEQ ID NO 9
<211> LENGTH: 172
<212> TYPE: PRT
<213> ORGANISM: Homo sapiens

<400> SEQUENCE: 9

Leu Glu Arg Gly Gly Glu Ala Ala Ala Ala Ala Ala Ala Ala Ala Ala
1               5                   10                  15

Ala Pro Gly Arg Gly Ser Glu Pro Val Thr Ile Ser Arg Ala Gly Asn
                20                  25                  30

Ala Gly Glu Leu Val Ser Pro Leu Leu Leu Pro Pro Thr Arg Arg Arg
                35                  40                  45
```

```
Arg Arg Arg His Ile Gln Gly Pro Gly Pro Val Leu Asn Leu Pro Ser
    50              55                  60

Ala Ala Ala Ala Pro Pro Val Ala Arg Ala Pro Glu Ala Ala Gly Gly
65              70                  75                  80

Gly Ser Arg Ser Glu Asp Tyr Ser Ser Ser Pro His Ser Ala Ala Ala
                85                  90                  95

Ala Ala Arg Pro Leu Ala Ala Glu Glu Lys Gln Ala Gln Ser Leu Gln
            100                 105                 110

Pro Ser Ser Ser Arg Arg Ser Ser His Tyr Pro Ala Ala Val Gln Ser
            115                 120                 125

Gln Ala Ala Ala Glu Arg Gly Ala Ser Ala Thr Ala Lys Ser Arg Ala
            130                 135                 140

Ile Ser Ile Leu Gln Lys Lys Pro Arg His Gln Gln Leu Leu Pro Ser
145                 150                 155                 160

Leu Ser Ser Phe Phe Phe Ser His Arg Leu Pro Asp
                165                 170

<210> SEQ ID NO 10
<211> LENGTH: 113
<212> TYPE: PRT
<213> ORGANISM: Apis mellifera

<400> SEQUENCE: 10

Met Leu Trp Glu Leu Met Gly Cys Ile Cys Phe Ser Cys Arg Arg Pro
1               5                   10                  15

Thr Gly Ser Arg Leu Asn Asn Lys Ile Ser Glu His Ile Ser Ala Ser
            20                  25                  30

Val Thr Pro Leu Met Val Cys Leu Glu Glu Gln Arg Gly Pro Glu Leu
        35                  40                  45

Gly Ser Cys Asp Ala Ser Ala Tyr Lys Pro Gln Pro Ser Met Ser Asn
    50                  55                  60

Thr Ile Ser Asn Met Lys Met Thr Asn Arg Ile Lys Gly Met Val Ser
65                  70                  75                  80

Lys Arg Arg Arg Arg Phe Thr Glu Asp Gly Phe Asp Leu Asp Leu Thr
                85                  90                  95

Tyr Ile Arg Asp Asn Leu Ile Ala Met Gly Phe Pro Ala Glu Lys Leu
                100                 105                 110

Glu

<210> SEQ ID NO 11
<211> LENGTH: 87
<212> TYPE: PRT
<213> ORGANISM: Caenorhabditis elegans

<400> SEQUENCE: 11

Met Val Thr Pro Pro Asp Val Pro Ser Thr Ser Thr Arg Ser Met
1               5                   10                  15

Ala Arg Asp Leu Gln Glu Asn Pro Asn Arg Gln Pro Gly Glu Pro Arg
            20                  25                  30

Val Ser Glu Pro Tyr His Asn Ser Ile Val Glu Arg Ile Arg His Ile
        35                  40                  45

Phe Arg Thr Ala Val Ser Ser Asn Arg Cys Arg Thr Glu Tyr Gln Asn
    50                  55                  60

Ile Asp Leu Asp Cys Ala Tyr Ile Thr Asp Arg Ile Ile Ala Ile Gly
65                  70                  75                  80

Tyr Pro Ala Thr Gly Ile Glu
```

<210> SEQ ID NO 12
<211> LENGTH: 264
<212> TYPE: PRT
<213> ORGANISM: Bos taurus

<400> SEQUENCE: 12

```
Met Arg Asp Gly Gly Gly Arg Ser Pro Ser Pro Leu Ser Ala Pro Val
1               5                   10                  15
Ser Ser Arg Gly Ala Ser Phe Ser Ala Ala Ser Pro Glu Arg Glu Gly
            20                  25                  30
Gly Ser Arg Gly Leu Gly Arg Glu Pro Ala Glu Ala Arg Arg Arg His
        35                  40                  45
Leu Pro Leu Leu Glu Arg Gly Gly Glu Ala Ala Ala Ala Ala Ala Ala
    50                  55                  60
Ala Ala Pro Gly Arg Gly Pro Glu Ser Pro Val Thr Ile Ser Arg Ala
65                  70                  75                  80
Gly Asn Ala Gly Glu Leu Val Ser Pro Leu Leu Pro Pro Thr Arg
                85                  90                  95
Arg Arg Arg Arg Arg His Ile Gln Gly Pro Gly Pro Val Leu Asn Leu
            100                 105                 110
Pro Ser Ala Ala Ala Pro Pro Leu Ala Arg Ala Pro Glu Ala Ala
        115                 120                 125
Gly Gly Gly Ser Arg Ser Glu Asp Tyr Ser Ser Pro His Ser Ala Ala
130                 135                 140
Ala Ala Ala Arg Pro Leu Ala Ala Glu Glu Lys Gln Ala Gln Ser Leu
145                 150                 155                 160
Gln Pro Ser Ser Ser Arg Arg Ser Ser His Tyr Pro Ala Ala Val Gln
                165                 170                 175
Ser Gln Ala Ala Ala Glu Arg Gly Ala Ser Ala Thr Ala Lys Ser Arg
            180                 185                 190
Ala Ile Ser Ile Leu Gln Lys Lys Pro Arg His Gln Gln Leu Leu Pro
        195                 200                 205
Ser Leu Ser Ser Phe Phe Phe Ser His Arg Leu Pro Asp Met Thr Ala
    210                 215                 220
Ile Ile Lys Glu Ile Val Ser Arg Asn Lys Arg Arg Tyr Gln Glu Asp
225                 230                 235                 240
Gly Phe Asp Leu Asp Leu Thr Tyr Ile Tyr Pro Asn Ile Ile Ala Asn
                245                 250                 255
Gly Phe Pro Ala Glu Arg Leu Glu
            260
```

<210> SEQ ID NO 13
<211> LENGTH: 217
<212> TYPE: PRT
<213> ORGANISM: Mus musculus

<400> SEQUENCE: 13

```
Leu His Leu Pro Leu Leu Glu Arg Gly Gly Glu Ala Ala Ala Ala Ala
1               5                   10                  15
Ala Ala Pro Gly Arg Gly Ser Glu Ser Pro Val Thr Ile Ala Arg Ala
            20                  25                  30
Gly Asn Ala Gly Glu Leu Leu Ser Pro Leu Leu Leu Pro Pro Thr Arg
        35                  40                  45
Arg Arg Arg Arg Arg Met Val Gln Gly Pro Gly Pro Val Leu Ser Leu
```

```
                50                  55                  60
Pro Ser Ala Ala Ala Pro Pro Leu Ala Arg Ala Pro Glu Ala Ala
 65                  70                  75                  80

Gly Gly Gly Ser Arg Cys Glu Asp Tyr Pro Ser Pro His Ser Ala
                 85                  90                  95

Ala Ser Ala Ala Arg Pro Leu Ala Ala Glu Glu Lys Gln Ala Gln Ser
                100                 105                 110

Leu Gln Pro Ser Ser Arg Arg Ser Ser His Tyr Pro Ala Ala Val
            115                 120                 125

Gln Gly Gln Ala Ala Glu Arg Gly Ala Ser Ala Thr Ala Lys Ser
        130                 135                 140

Arg Ala Ile Ser Ile Leu Gln Lys Lys Pro Arg His Gln Gln Leu Leu
145                 150                 155                 160

Pro Ser Leu Ser Ser Phe Phe Phe Ser His Arg Leu Pro Asp Met Thr
                165                 170                 175

Ala Ile Ile Lys Glu Ile Val Ser Arg Asn Lys Arg Tyr Gln Glu
                180                 185                 190

Asp Gly Phe Asp Leu Asp Leu Thr Tyr Ile Tyr Pro Asn Ile Ile Ala
            195                 200                 205

His Gly Phe Pro Ala Glu Arg Leu Glu
    210                 215

<210> SEQ ID NO 14
<211> LENGTH: 161
<212> TYPE: PRT
<213> ORGANISM: Pan troglodytes

<400> SEQUENCE: 14

Met Arg Asp Gly Gly His Gly Pro Glu Pro Leu Ser Ala Pro Pro
  1               5                  10                  15

Val Ala Arg Ala Pro Glu Ala Ala Gly Gly Ser Arg Ser Glu Asp
             20                  25                  30

Tyr Ser Ser Ser Pro His Ser Ala Ala Ala Ala Arg Pro Leu Ala
         35                  40                  45

Ala Glu Glu Lys Gln Ala Gln Ser Leu Gln Pro Ser Gly Ser Arg Arg
     50                  55                  60

Ser Ser His Tyr Pro Ala Ala Val Gln Ser Gln Ala Ala Glu Arg
 65                  70                  75                  80

Gly Ala Ser Ala Thr Ala Lys Ser Arg Ala Ile Ser Ile Leu Gln Lys
                 85                  90                  95

Lys Pro Arg His Gln Gln Leu Leu Pro Ser Leu Ser Ser Phe Phe Phe
                100                 105                 110

Ser His Arg Leu Pro Asp Met Thr Ala Ile Ile Lys Glu Ile Val Ser
            115                 120                 125

Arg Asn Lys Arg Tyr Gln Glu Asp Gly Phe Asp Leu Asp Leu Thr
        130                 135                 140

Tyr Ile Tyr Pro Asn Ile Ile Ala Met Gly Phe Pro Ala Glu Arg Leu
145                 150                 155                 160

Glu

<210> SEQ ID NO 15
<211> LENGTH: 216
<212> TYPE: PRT
<213> ORGANISM: Homo sapiens

<400> SEQUENCE: 15
```

Leu Glu Arg Gly Gly Glu Ala Ala Ala Ala Ala Ala Ala
1               5                   10                  15

Ala Pro Gly Arg Gly Ser Glu Ser Pro Val Thr Ile Ser Arg Ala Gly
            20                  25                  30

Asn Ala Gly Glu Leu Val Ser Pro Leu Leu Pro Pro Thr Arg Arg
            35                  40                  45

Arg Arg Arg Arg His Ile Gln Gly Pro Gly Pro Val Leu Asn Leu Pro
50                  55                  60

Ser Ala Ala Ala Pro Pro Val Ala Arg Ala Pro Glu Ala Ala Gly
65                  70                  75                  80

Gly Gly Ser Arg Ser Glu Asp Tyr Ser Ser Pro His Ser Ala Ala
                85                  90                  95

Ala Ala Ala Arg Pro Leu Ala Ala Glu Glu Lys Gln Ala Gln Ser Leu
            100                 105                 110

Gln Pro Ser Ser Ser Arg Arg Ser Ser His Tyr Pro Ala Ala Val Gln
        115                 120                 125

Ser Gln Ala Ala Ala Glu Arg Gly Ala Ser Ala Thr Ala Lys Ser Arg
130                 135                 140

Ala Ile Ser Ile Leu Gln Lys Lys Pro Arg His Gln Gln Leu Leu Pro
145                 150                 155                 160

Ser Leu Ser Ser Phe Phe Phe Ser His Arg Leu Pro Asp Met Thr Ala
                165                 170                 175

Ile Ile Lys Glu Ile Val Ser Arg Asn Lys Arg Arg Tyr Gln Glu Asp
            180                 185                 190

Gly Phe Asp Leu Asp Leu Thr Tyr Ile Tyr Pro Asn Ile Ile Ala Met
        195                 200                 205

Gly Phe Pro Ala Glu Arg Leu Glu
    210                 215

<210> SEQ ID NO 16
<211> LENGTH: 208
<212> TYPE: PRT
<213> ORGANISM: Artificial
<220> FEATURE:
<223> OTHER INFORMATION: Consensus sequence

<400> SEQUENCE: 16

Leu Glu Arg Gly Gly Ala Ala Ala Ala Ala Ala Pro Gly Arg Gly
1               5                   10                  15

Glu Ser Pro Val Thr Ile Ser Arg Ala Gly Asn Ala Gly Glu Leu Val
            20                  25                  30

Ser Pro Leu Leu Leu Pro Pro Thr Arg Arg Arg Arg Arg His Ile
        35                  40                  45

Gln Gly Pro Gly Pro Val Leu Leu Pro Ser Ala Ala Ala Pro Pro
    50                  55                  60

Leu Ala Arg Ala Pro Glu Ala Ala Gly Gly Gly Ser Arg Ser Glu Asp
65                  70                  75                  80

Tyr Ser Ser Pro His Ser Ala Ala Ala Ala Arg Pro Leu Ala Ala
                85                  90                  95

Glu Glu Lys Gln Ala Gln Ser Leu Gln Pro Ser Ser Ser Arg Arg Ser
            100                 105                 110

Ser His Tyr Pro Ala Ala Val Gln Ser Gln Ala Ala Ala Glu Arg Gly
        115                 120                 125

Ala Ser Ala Thr Ala Lys Ser Arg Ala Ile Ser Ile Leu Gln Lys Lys
130                 135                 140

```
Pro Arg His Gln Gln Leu Leu Pro Ser Leu Ser Ser Phe Phe Phe Ser
145                 150                 155                 160

His Arg Leu Pro Asp Met Thr Ala Ile Ile Lys Glu Ile Val Ser Arg
                165             170                 175

Asn Lys Arg Arg Tyr Gln Glu Asp Gly Phe Asp Leu Asp Leu Thr Tyr
            180             185             190

Ile Tyr Pro Asn Ile Ile Ala Met Gly Phe Pro Ala Glu Arg Leu Glu
        195             200             205

<210> SEQ ID NO 17
<211> LENGTH: 71
<212> TYPE: PRT
<213> ORGANISM: Homo sapiens

<400> SEQUENCE: 17

Leu Glu Arg Gly Gly Glu Glu Ala Ala Ala Ala Ala Ala Ala Ala Ala
1               5                   10                  15

Ala Ala Pro Gly Arg Gly Ser Glu Ser Pro Val Thr Ile Ser Arg Ala
                20                  25                  30

Gly Asn Ala Gly Glu Leu Val Ser Pro Leu Leu Leu Pro Pro Thr Arg
            35                  40                  45

Arg Arg Arg Arg Arg His Ile Gln Gly Pro Gly Pro Val Leu Asn Leu
    50                  55                  60

Pro Ser Ala Ala Ala Ala Pro
65                  70
```

USE OF *PTEN*-LONG LEADER SEQUENCE FOR TRANSMEMBRANE DELIVERY OF MOLECULES

This application is a §371 national stage of PCT International Application No. PCT/US2011/025312, filed Feb. 17, 2011, claiming the benefit of U.S. Provisional Application No. 61/338,377, filed Feb. 17, 2010, the contents of each of which are hereby incorporated by reference in their entirety.

The work disclosed herein was made with government support under grant no. CA082783 from the National Cancer Institute. Accordingly, the U.S. Government has certain rights in this invention.

Throughout this application, various publications are referenced in parentheses by first author and year. Full citations for these references may be found at the end of the specification immediately preceding the claims. The disclosures of these publications in their entireties are hereby incorporated by reference into this application to more fully describe the state of the art to which this invention pertains.

REFERENCE TO SEQUENCE LISTING

This application incorporates-by-reference nucleotide and/or amino acid sequences which are present in the file named "120814_0575_81351_A_PCT_US_Substitute_Sequence_ Listing_BI.txt," which is 34.9 kilobytes in size, and which was created Aug. 14, 2012 in the IBM-PC machine format, having an operating system compatibility with MS-Windows, which is contained in the text file filed Aug. 14, 2012 as part of this application.

BACKGROUND

The PTEN tumor suppressor (see WO98/34624 which is hereby incorporated by reference in its entirety) is a cytoplasmic phosphatase which dephosphorylates the important second messenger phosphatidylinositol 3,4,5-triphosphate (Maehama and Dixon 1998). This activity downregulates the many oncogenic signals initiated by PIP3 activation of Akt including anti-apoptotic pathways, cell cycle progression and increasing cell metabolism (Sulis and Parsons 2003). The role of PTEN in cancer is evident from its frequent loss, either genetically or functionally, in many different tumor types (Bonneau and Longy 2000). Originally discovered as deleted in glial cancers, it has since been implicated in tumorigenesis of the prostate, breast, endometrium, melanocytes, kidneys and lungs. Germline mutations in PTEN were also linked to inherited cancer predisposition syndromes such as Cowden's Syndrome (Eng 2003). Mouse models of PTEN loss have recapitulated its role as an tumor suppressor both in the heterozygous mouse and tissue specific knockouts in many different tissue types (Di Cristofano, Pesce et al. 1998; Kwabi-Addo, Giri et al. 2001; Petrocelli and Slingerland 2001; You, Castrillon et al. 2002; Fraser, Zhu et al. 2004).

The PTEN protein contains an N-terminal dual specificity phosphatase domain, and a C-terminal C2 phospholipid binding domain, followed by an unstructured tail of regulatory importance because of the phosphorylation sites found within (Lee, Yang et al. 1999; Vazquez, Ramaswamy et al. 2000; Torres and Pulido 2001; Vazquez, Grossman et al. 2001). PTEN protein is mostly cytoplasmic however there is increasing evidence for a PTEN presence in the nucleus, a localization which is regulated by the monoubiquitination of the protein by NEDD4-1 (Baker 2007; Wang, Trotman et al. 2007).

Ribosome scanning of the 5'UTR precedes translation initiation which occurs at the start codon, AUG. Though the actual means by which the ribosome decides the proper start codon remains incompletely understood, there are certain properties of both the mRNA itself and the sequence which will dictate where the pre-initiation complex will slow its scanning and start to translate. The classic "Kozak sequence" CCACC<u>ATG</u>G, where the underlined ATG is the initiation codon, has been shown to be the most favorable sequence context for initiation (Kozak 1991). mRNA secondary structure also promotes initiation probably by an actual slowing of the scanning of the pre-initiation complex which requires a helicase to melt secondary structures prior to reading (Kozak 1990).

In certain transcripts, translation initiation can occur from non-AUG codons. This usually comprises only a minor percentage of the total protein translated from a transcript and the result is a mixed species of proteins varying at their N-termini. Kozak delineated the efficiencies of translation initiation from non-AUG codons and found that GUG and CUG were both capable of initiating translation in vitro however far less efficiently (Kozak 1989). Further research has shown that the availability of methionine can alter the promiscuity of translation initiation through a mechanism that remains unclear, but probably involves the phosphorylation of eIF2, a component of the 43S pre-initiation complex, by a nutrient sensitive kinase (Hershey 1991; Hann 1994).

A number of proteins have been shown to be translated from alternate initiation codons. The transcription factor, c-myc, has an alternate upstream CUG initiation codon which when translated, adds 14 amino acids to the N-terminus of the protein (Hann and Eisenman 1984). This alternate isoform has been shown to be selectively disrupted in Burkitt's lymphoma (Hann, King et al. 1988). In tissue culture the longer form of myc is predominantly transcribed at high cell densities when methionine is at a low concentration (Hann, Sloan-Brown et al. 1992). Further studies have revealed that the longer form of c-myc is growth inhibitory and has a different set of transcriptional targets than the classic c-myc protein (Hann, Dixit et al. 1994). (Florkiewicz and Sommer 1989) (Prats, Kaghad et al. 1989).

Additionally, it is known that the actual subcellular localization of a protein can be dictated by alternate initiation codons. In the case of the mouse proto-oncogene int-2 alternate initiation from an upstream CUG codon encodes a nuclear localization while the AUG codon encodes a signal peptide for localization to the secretory pathway (Acland, Dixon et al. 1990). A similar phenomenon was described in the human FGF3, in which the protein translated from AUG is destined for the secretory pathway while the protein translated from an upstream CUG is localized to the nucleus (Kiefer, Acland et al. 1994). Furthermore, in some eukaryotic proteins, such as TEF-1 and PRPS-3, the protein is completely initiated from a CUG codon (Taira, Iizasa et al. 1990; Xiao, Davidson et al. 1991).

Proteins that are destined for secretion are targeted to the endoplasmic reticulum by a stretch of hydrophobic amino acids called a signal peptide (Blobel, Walter et al. 1979). Usually found at the N-termini of proteins, the signal peptide binds the signal recognition particle (SRP) upon translation and causes the ribosome to halt and translocate to the rough endoplasmic reticulum where it binds the SRP receptor. Once the ribosome docks, the SRP-SRP receptor complex is released and translation resumes through the lumen of the ER through the Sec61 translocon. The signal peptide is then cleaved off in the case of soluble proteins releasing the protein from the Sec translocon. In the case of proteins spanning a membrane, the transmembrane helix serves as a signal peptide for ER translocation. These proteins are modified extensively by glycosylation in the golgi and are shuttled to the plasma membrane in secretory vesicles (Alberts 2002).

There are a number of secreted proteins that have been shown to be important in cancer. The Wnt signaling pathway for example has been shown to be altered in lung cancer. Wnt is a secreted ligand for the family of Frizzled receptors. Wnt activation of frizzled causes disheveled to dissociate the □-catenin degradation complex, which includes APC, allowing for levels of □-catenin to rise and translocate to the nucleus where it can interact and transactivate the TCF transcription factor. Inactivating mutations in APC and activating mutations in □-catenin have been detailed in both inherited and sporadic colon cancer. Additionally, a number of extracellular ligand antagonists such as SFRP and Wnt-5a compete for the same Frizzled receptors as Wnt. Both have been shown to be tumor suppressors; the SFRP knockout mouse develops lymphoid tumors and epigenetic silencing of Wnt-5a has been detected in melanomas.

As disclosed herein, the leader sequence of a novel differentially translated protein, named PTEN-long, is able to act as a cell penetrating peptide akin to HIV TAT.

SUMMARY OF THE INVENTION

A composition comprising (i) a peptide comprising consecutive amino acid residues 22-173 of the sequence set forth in SEQ ID NO:1, or a portion of amino acid residues 22-173 of SEQ ID NO:1, for the transport of a cargo molecule across a biological membrane and (ii) the cargo molecule, wherein the cargo molecule is not a peptide comprising amino acid residues having the sequence set forth in SEQ ID NO:4.

A method for delivering a cargo molecule into a cell, comprising contacting the cell with a composition comprising (i) a peptide comprising consecutive amino acid residues 22-173 of the sequence set forth in SEQ ID NO: 1, or a portion of the amino acid residues set forth in SEQ ID NO:1, for the transport of the cargo molecule across a biological membrane and (ii) the cargo molecule, wherein the cargo molecule is not a peptide comprising amino acid residues having the sequence set forth in SEQ ID NO 4, under conditions permitting the entry of the cargo molecule into the cell.

A method for treating a tumor in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule, wherein the cargo molecule is not a peptide comprising amino acid residues having the sequence set forth in SEQ ID NO:4 in an amount effective to treat the tumor in the subject.

A method for treating cancer in a subject comprising administering to the subject an amount of a composition comprising a peptide comprising amino acid residues 22-173 of SEQ ID NO:1, or a portion of amino acid residues 22-173 of SEQ ID NO:1, conjugated to a to a cargo molecule, wherein the cargo molecule is not a peptide comprising amino acid residues having the sequence set forth in SEQ ID NO:4 in an amount effective to treat the cancer in the subject.

A method for treating a metabolic disorder in a subject, wherein the metabolic disorder is characterized by a deficiency in a metabolic enzyme comprising administering to the subject an amount of a composition comprising a peptide comprising amino acid residues 22-173 of SEQ ID NO:1, or portion of amino acid residues 22-173 of SEQ ID NO:1, conjugated to the metabolic enzyme in an amount effective to treat the metabolic disorder in the subject.

A method for treating diabetes in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule in an amount effective to treat the diabetes in the subject.

A method for treating a cardiovascular disease in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule in an amount effective to treat the cardiovascular disease in the subject.

BRIEF DESCRIPTION OF THE FIGURES

FIG. 3. Alignment of N-termini of PTEN Orthologs. PTEN protein sequences from indicated species were aligned using BLOSUM62 score matrix on Vector NTI (Invitrogen). Extended N-terminal sequence for both *Homo sapiens* (SEQ ID NO:15) and *Mus musculus* (SEQ ID NO:13) (asterix) were translated from published mRNA using a CUG alternate initiation codon at −519 (*H. sapiens*) and −520 (*M. musculus*) from the canonical AUG start codon using ORFinder (NCBI). mRNA sequences from *Homo sapiens* (NM_000314) and *Mus musculus* (NM_008960). *Apis mellifera* sequence (SEQ ID NO:10) was obtained from Baylor College of Medicine Honey Bee Genome Project. Protein sequence for *Caenorhabditis elegans* PTEN (SEQ ID NO:11) (Daf-18) was downloaded from Wormbase. *Bos Taurus* (XM_613125) (SEQ ID NO:12) and *Pan troglodytes* (SEQ ID NO:14) (XP_521544) were downloaded from NCBI. Consensus sequence is SEQ ID NO:16.

PTEN-long can be seen in cells only overexpressing the 5'ATR. A background band observed in U87 cells is present at the bottom of the blot.

Figure 5:
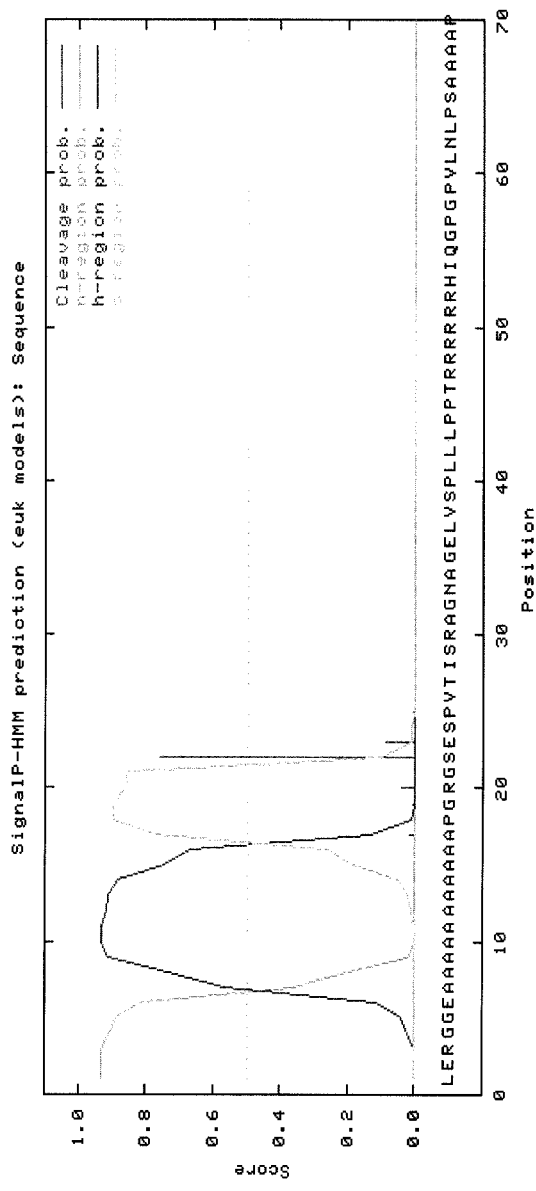

FIG. 5. Signal Peptide Prediction. PTEN 5'UTR sequence was translated and inputted into SignalIP3.0. Hidden markov model for eukaryotic signal peptides was used for prediction. The N-region denotes the positively charged N-terminal sequence of the signal peptide. The H-region is the hydrophobic core of the signal peptide. The C-region is mildly polar region marked by a proline which usually breaks the helix of the hydrophobic core. The cleavage probability is predictive of a cleavage site to release the signal peptide, allowing the protein to be released into the lumen of the ER. (Dalbey and Heijne, 2002). Cleavage is predicted to occur at position 21. Sequence shown is SEQ ID NO:17.

Figure 6:
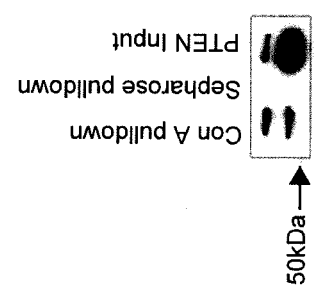

FIG. 6. Concanavalin A pulldown. HEK293 cells were lysed and concanavalin sepharose was used to pulldown glycosylated proteins. Eluates were resolved by SDS-PAGE and immunoblotted for PTEN (6H2.1). An enrichment in the PTEN-long can be observed in the pulldown versus input. Note enrichment of longer PTEN band. PTEN has multiple potential O-glycosylation sites, but only one N-glycosylation site. We used the lectin concanavalin-A, which binds sugar moieties, in a pulldown assay to determine whether a portion of the PTEN complement in HEK293 cells is glycosylated. We were able to purify a mixture of PTEN that was approximately 50% PTEN-long, a vast enrichment of PTEN-long over normal PTEN. This shows that PTEN-long is glycosylated and that either the cytoplasmic 55 kDa form of PTEN is glycosylated or that PTEN-long is cleaved extracellularly.

Figure 7:
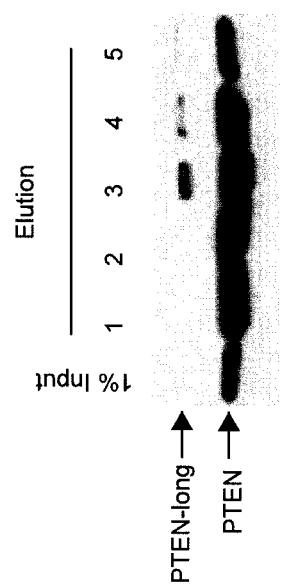

FIG. 7. PTEN and PTEN-β bind heparan. Mouse liver extract was passed through a 1 ml HiTrap Heparin sepharose (Amersham) column. The column was washed with 500 mM NaCl, and proteins were eluted with sequential column volumes of 1M NaCl. Fractions were analyzed by SDS-PAGE for PTEN using a PTEN monoclonal antibody. PTEN has previously been shown to have an affinity for highly negatively charged species, a property of PTEN which leads to its preference of the highly anionic PtdIns(3,4,5)P3 (Das, Dixon et al. 2003). As heparan is one of the most negatively charged biological molecules, we postulated that heparan was actually mediating the binding of PTEN to the extracellular matrix. Using protein extracts from mouse livers, we discovered that PTEN binds heparan with high affinity. Furthermore, continuous elution of PTEN from a heparin agarose column using 1M NaCl, also eluted PTEN-long.

Figure 8:
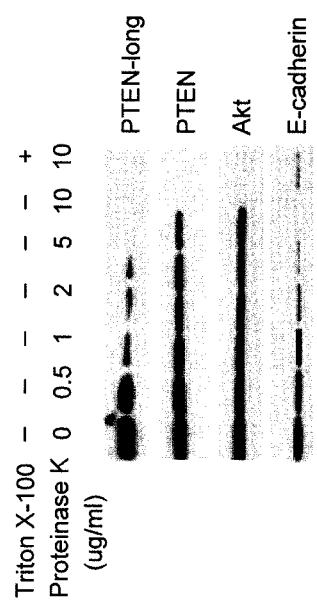

FIG. 8. Protease Protection Assay. HEK293 cells were resuspended in increasing concentrations of proteinase K. Triton at a final concentration of 0.2% was added to the reaction containing the highest concentration of Proteinase K. The reaction was stopped with PMSF and cell lysates were made in laemlli buffer. Lysates were resolved by SDS-PAGE on a 8% polyacrylamide gel and immunoblotted for PTEN (6H2.1), AKT, E-cadherin. The larger band of the PTEN immunoblot is designated PTEN-long. These data show that E-Cadherin and PTEN-long are largely on the cell surface.

Figure 9:
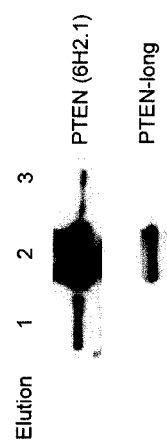

FIG. 9. High salt elution of PTEN and PTEN-long from heparin affinity purification of conditioned media. PTEN and PTEN-long can be eluted from a HiTrap Heparin (Amersham) column after affinity purification from conditioned media. Both a monoclonal antibody to the tail of PTEN (above) and an antibody specific to amino acids translated in the 5'ATR recognize a protein band of approximately 55 kDa in mass.

Figure 10:
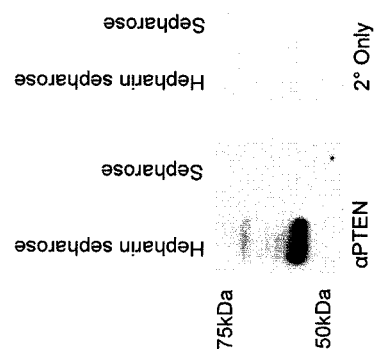

FIG. 10. Purification of PTEN from human serum. Human serum from AB blood was precleared of antibodies with protein A/G and subject to heparin sepharose. Eluates were resolved by SDS-PAGE and immunoblotted for PTEN or with secondary alone to control for heavy chain contamination.

FIGS. 11A-11C. Anti-Angiogenic activity of PTEN-long. (A) PTEN-long is expressed in a subset of vessels and capillaries in the developing retina. This expression pattern is in stark contrast to that of the canonical form of PTEN and is consistent with a role for PTEN-long in induction of vascular regression that occurs in these regions. This correlation is strengthened by the marked up-regulation of PTEN-long, when this process of vascular regression has been induced by hyper-oxia as per the western blot of whole retina lysates on the top right (B), and by the loss of PTEN-long in endothelial cells under hypoxic conditions (C). These findings indicate the usefulness of PTEN-long as an anti-angiogenic therapy, for example in diabetic retinopathy, as well as hyper-proliferative vascular disorders. Arrows indicate CD34 and PTEN-long positive tissue (blood vessels).

Figure 12:
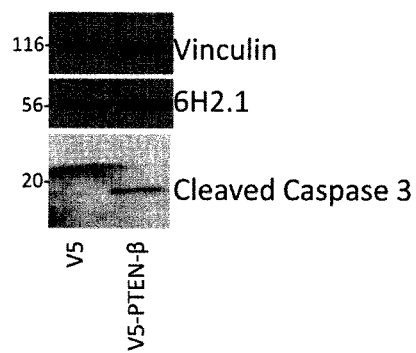

FIG. 12. Pro-apoptotic activity of PTEN-Long. Apoptosis was induced in MCF-10A mammary epithelial cells that were treated with purified PTEN-long for 24 hrs as indicated. Caspase 3 cleavage was indicative of apoptotic activity.

Figure 13:
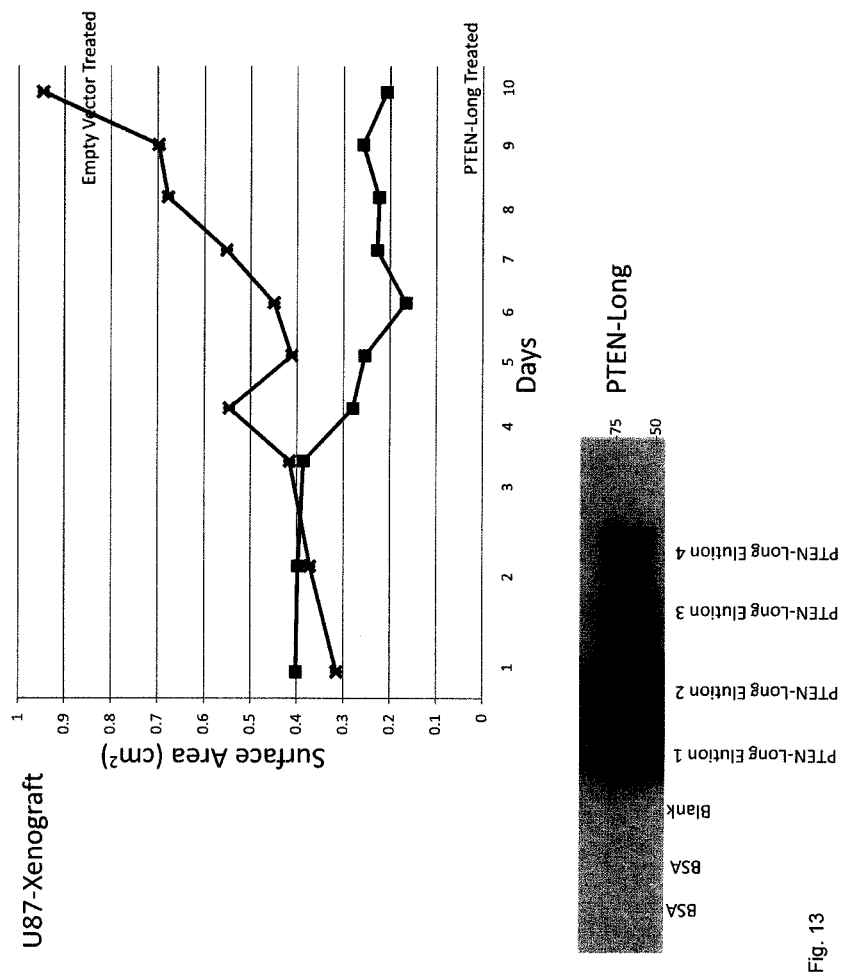

FIG. 13. Treatment of Mice with PTEN-Long. Graph of Tumor size as gauged by Caliper measurements over ten days of treatment, with either PTEN-long or an Empty Vector Control. 293 cells were transfected with ATG/ATG PTEN-long in the pcDNA3.1 His V5 vector. Cytoplasmic lysates were made 48 hr after transfection and passed over V5-antibody beads and eluted with V5 peptide. Western blot of the V5-bead purification eluates are shown below. Initial observation that PTEN-long could be used to treat Tumors. Xenografts were established using U87 glioblastoma cells (1 million) injected into the mammary fat pad of a scid mouse. Treatment was initiated approximately two weeks after transplantation.

Figure 14:
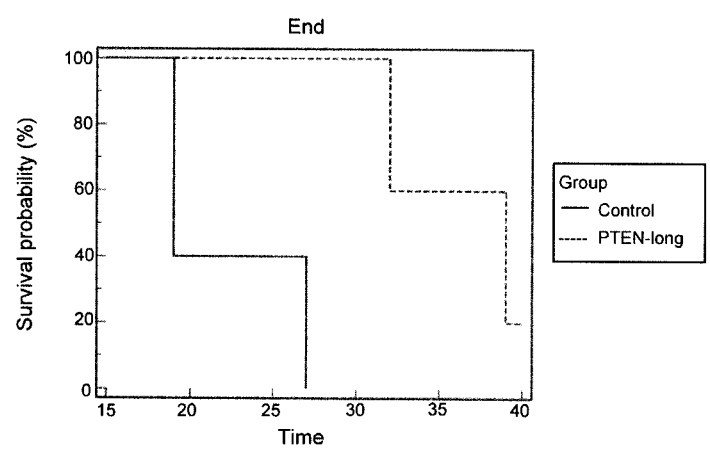

FIG. 14. Results of Treatment of Mice with PTEN-long. Graph shows the surviving fraction of mice (in days) treated with control and injections of PTEN-long for 14 days.

Figure 15:
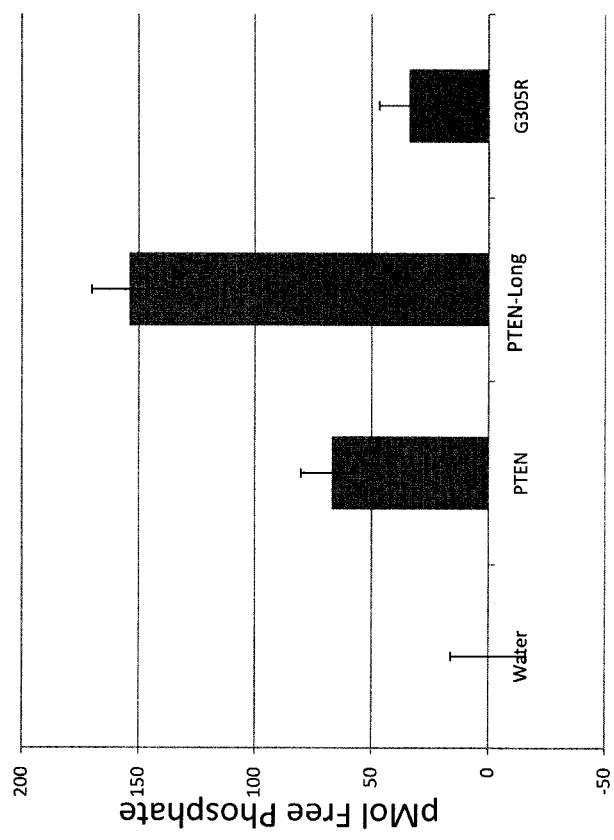

FIG. 15. Indicated constructs for PTEN (PTENorf lacking the 5'UTR), PTEN-long, and PTEN-long with a G to R mutation at amino acid 305, which is comparable to G129R mutation in PTENorf, were transfected into 293 cells. Using purified protein from these cells it was shown that PTEN-long is an active phosphatase, and that the PTEN-long G305R mutant (which is G129R in PTEN) reduces phosphatase activity.

Figure 16:
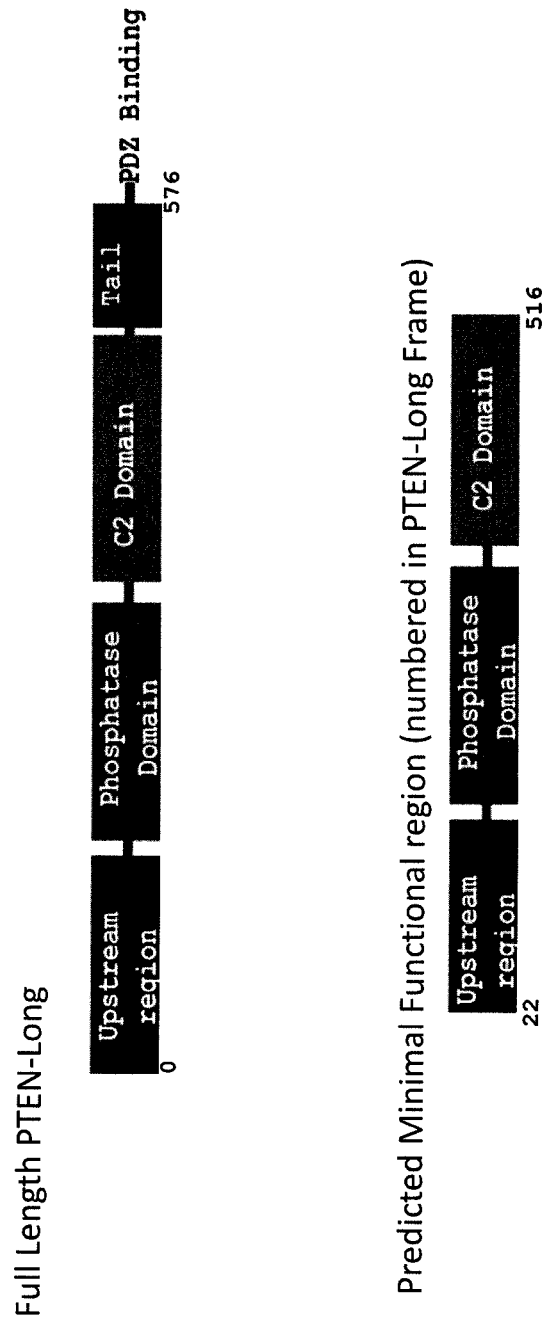

FIG. 16. Phosphatase activity is essential for PTEN-long activity is shown in the experiments with the PTEN-long (G305R) mutant. Based upon the PTEN literature it is known that truncations made inside the C2 domain destabilize the protein, and based upon the PTEN crystal structure it is believed interactions between the C2 domain and the phosphatase domains are critical for phosphatase activity. Therefore the minimal domain for PTEN-long activity at the C-terminus will require the C2 domain but not the tail. At the N-terminus the predicted cleavage site is at amino acid 21, and therefore the functional region of the protein is within this region. In regard to this it is important to note that when U87 tumors were treated in parallel with PTEN or with PTEN-long, no significant effect was observed from the PTEN treatment, only PTEN-long treatment.

Figure 17:
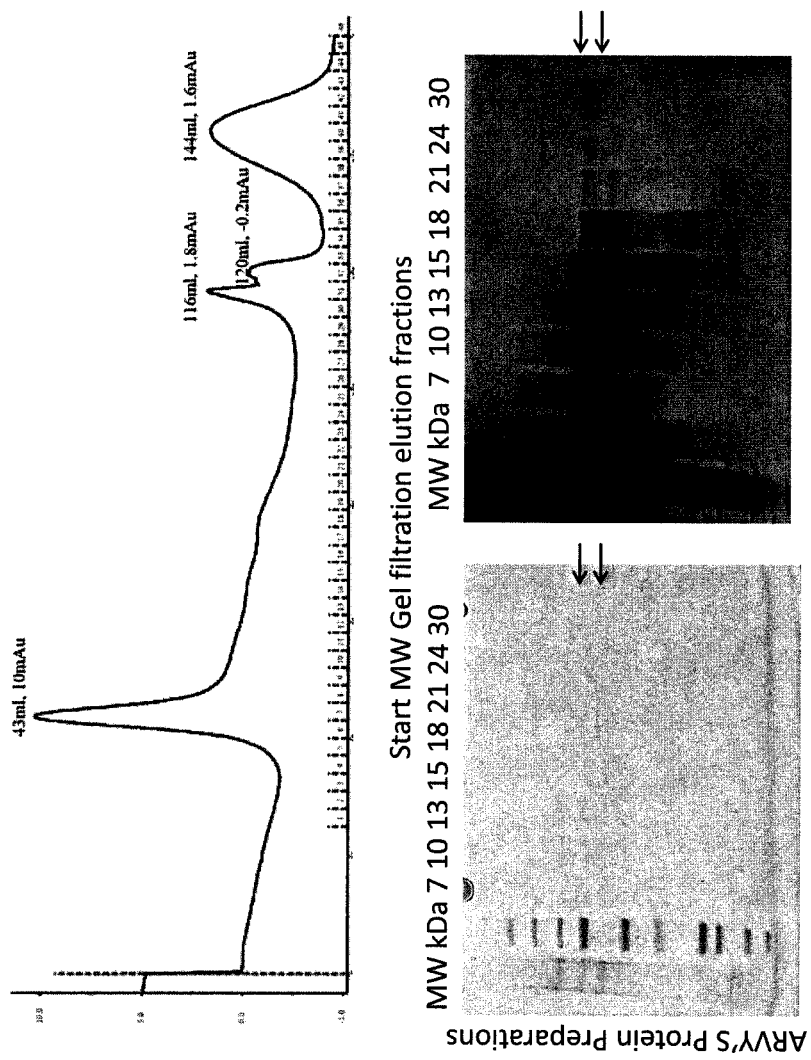

FIG. 17. Purification of PTEN-long from 293 cells transfected with ATG/ATG-PTEN long in the pcDNA3.1 expression vector with His and V5 tags. After Ni+ column elution, eluate was resolved in a gel filtration column. OD280 is shown with blue line. PTEN-long is enriched in fractions 7-18. Yield for this experiment was approximately 1 mg. Arrows indicate PTEN-long and altered migrating PTEN-long products.

FIGS. 18A-18B. (A) Dose Response of LNCaP prostate cancer cells to PTEN-long purified protein using cell death as a readout (Protein was purified by ARVYS). 1× equals 0.33 microgram per ml. Cells were treated in media without growth factors. After 24 hr, cells were washed with serum free media and lysed in Laemmli sample buffer. Western blots for indicated proteins were performed. (B) U87 glioblastoma cells treated with PTEN-long, PTEN-long(G305R) or a Mock control show induction of apoptosis as indicated by cleavage of PARP and down-regulation of pAKT signal at serine 473. These data further confirm that PTEN-long can induce apoptosis and reduce PI3K/AKT signaling.

Figure 19:
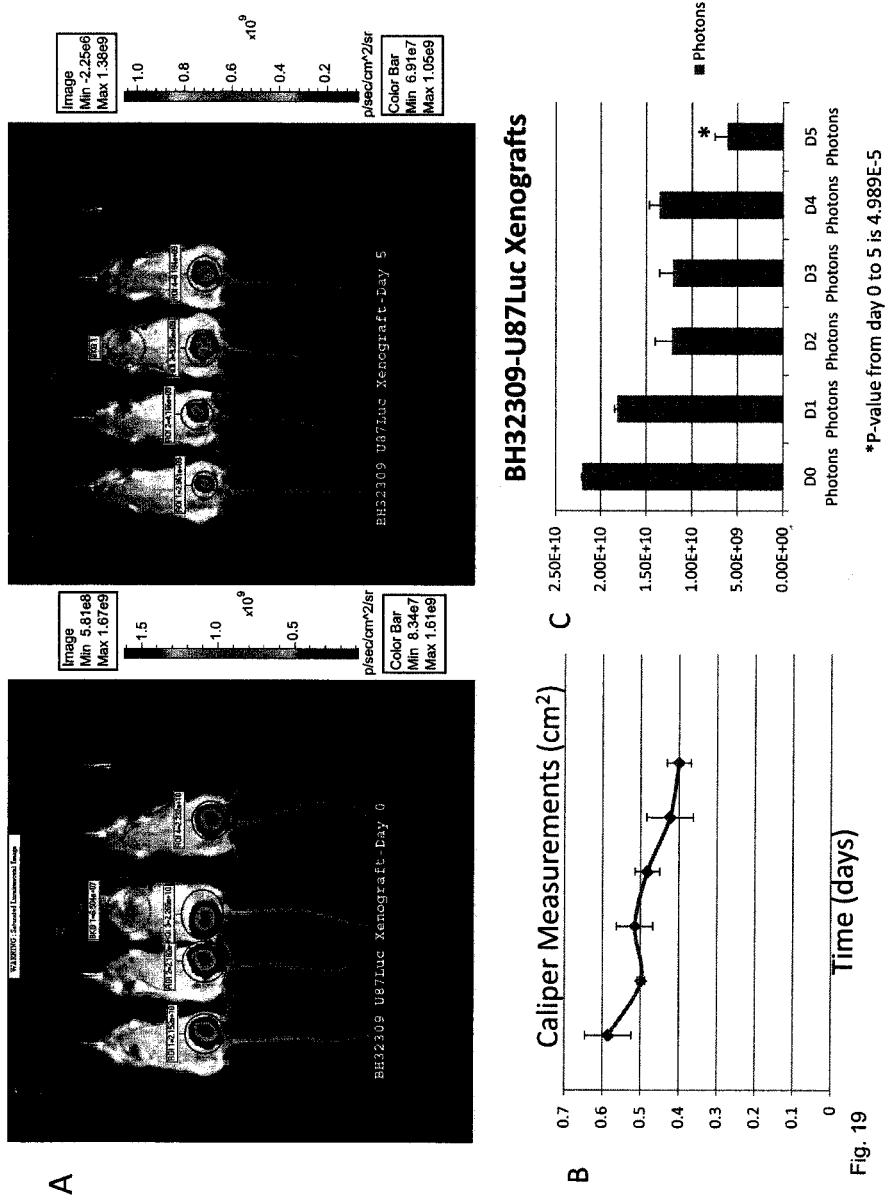

FIGS. 19A-19C. The AKTA purified PTEN-long protein was able to reduce tumor size over a five day period, as measured by both calipers and using a luciferase reporter in conjunction with a xenogen live animal imaging system. Mice were given ~0.05 mg PTEN-long per day for five days. Xenografts were established with 1 million U87 glioblastoma cells injected into the mammary fat pad that express luciferase due to infection with FUW-luciferase-neo. Mice were injected with luciferin intraperitoneally 10 minutes before imaging with the Xenogen Imaging System. (A) Luciferase measurements for 4 mice before (left panel) and on the fifth day of treatment (right panel). (B) Caliper measurements in $cm^2$ before and during the 5 days of treatment. (C) Photons detected by Xenogen system as imaged in panel. Standard error for four mice in cohort is shown. Student t-test for photons detected from day 0 to day 5.

Figure 20:
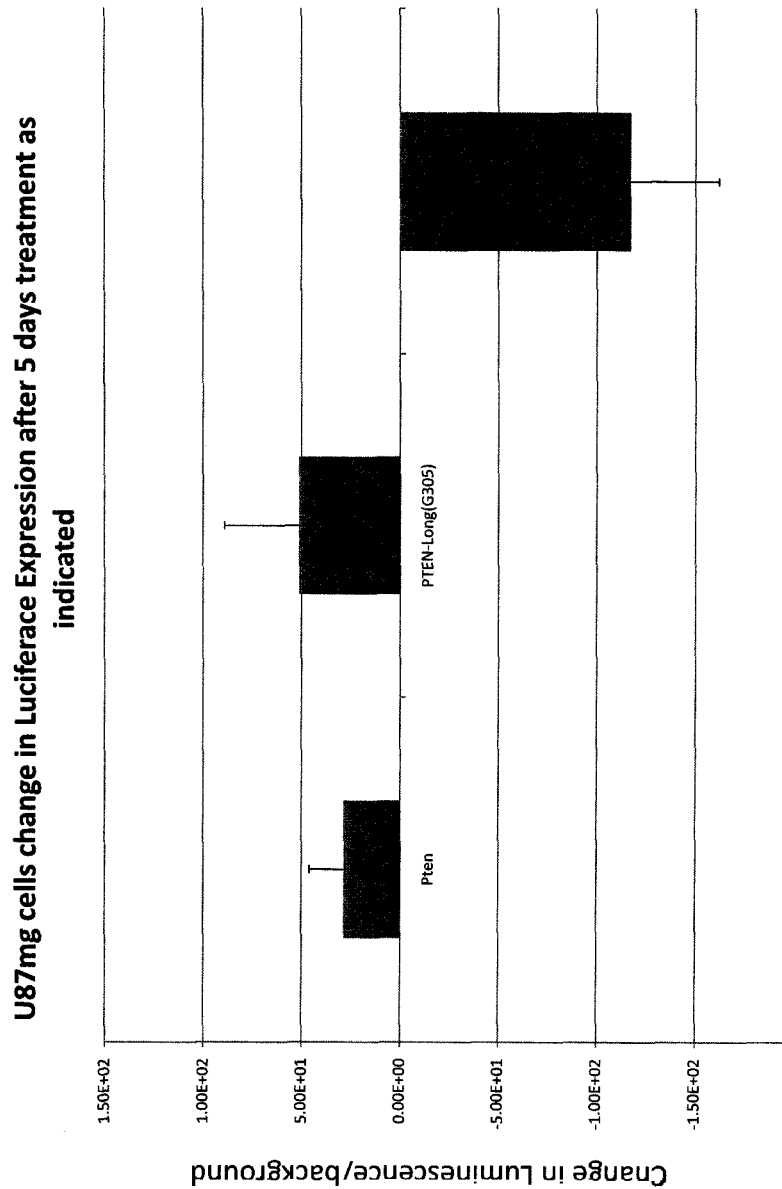

FIG. 20. In an independent experiment, U87 tumors were allowed to grow to 1.5 $cm^2$ before treatment with PTEN (orf-403 amino acids; n=5), PTEN-long (G305R; n=5) or wild type PTEN-long (n=4). After 5 days of treatment the average change luminescence shows a significant decrease for PTEN-long treated mice, but no decrease for the PTEN or PTEN-long(G305R) treated cohorts. Reduced luminescence correlated with reduced tumor size. These data demonstrate that PTEN-long requires the 5'ATR and phosphatase activity to function.

FIGS. 21A-21C. Analysis of PTEN-long-treated U87 xenografts demonstrates activation of apoptosis and inhibition of PI3K signaling. Tumors were treated for 5 days as above. (A) PTEN-long wild type and G305R treated tumors were harvested after 5 days of indicated treatment and lysed for western analysis. Wild type protein for PTEN-long was able to reduce FOXO and AKT phosphorylation and activate caspase-3 cleavage. (B) Representative tumors treated for 5 days as indicated were fixed in formalin and paraffin embedded. Sections were stained for an antibody that detects cleaved caspase-3, a marker of apoptosis. PTEN-long treated cells had a significant increase in percent of apoptotic cells P=0.0419, student's t-test. (C) Representative images of cleaved caspase-3 staining.

Figure 22:
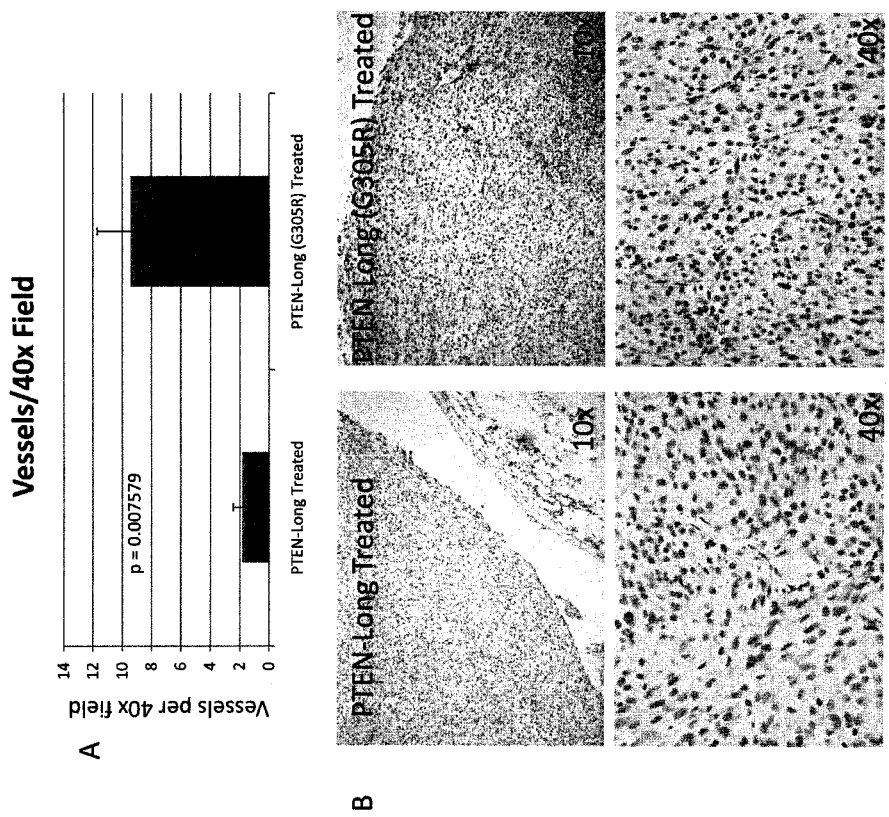

FIGS. 22A-22B. In the same tumor treated with PTEN-long for 5 days the number of blood vessels was greatly reduced. PTEN-long wild type and G305R treated tumors were harvested after 5 days of indicated treatment and were fixed in formalin and paraffin embedded. Sections were stained for an antibody that detects CD31, a marker of endothelial cells that line blood vessels. (A) PTEN-long treated cells had a significant reduction in the in the number of vessels per field of view (40× objective) P=0.007579, student's t-test. (B) Representative images of CD31 staining.

Figure 23:
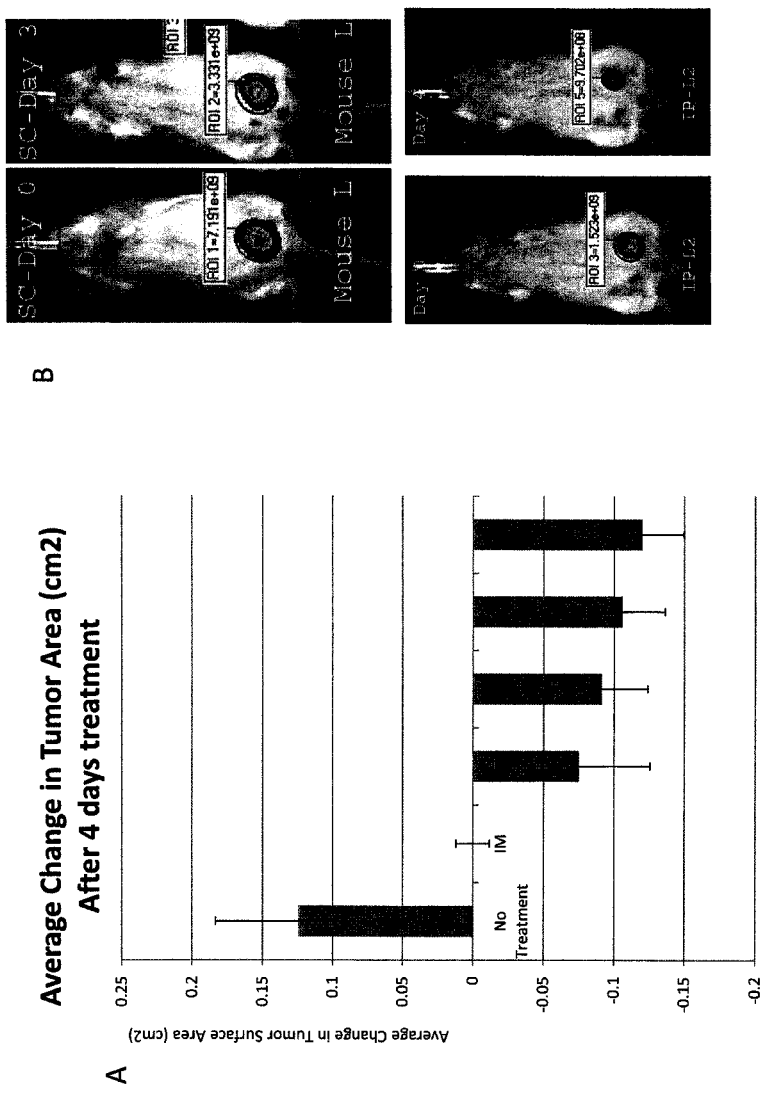
Figure 24:
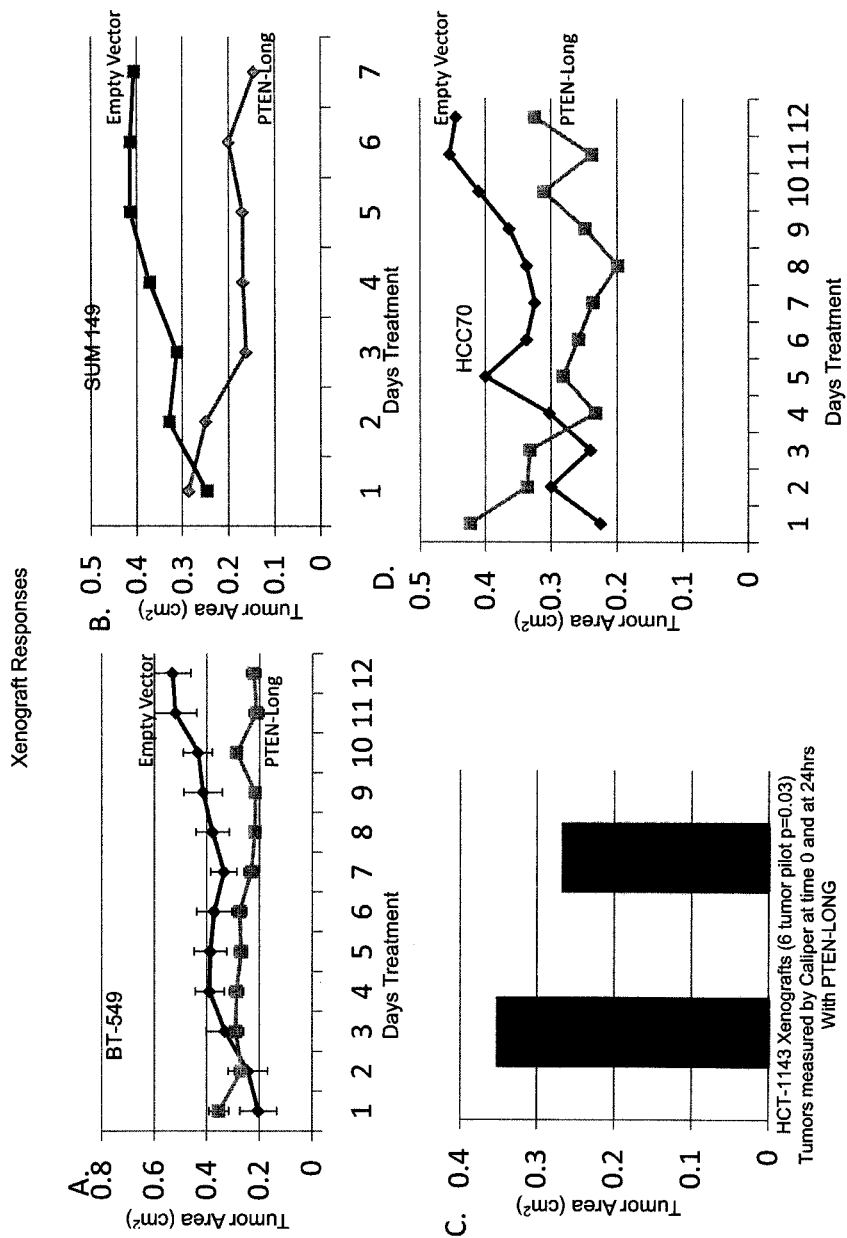

FIGS. 23A-23B. U87 xenografts were established in six groups (n=3/group) and were treated for four days with PTEN-long via Intra-Muscular (IM), Intra peritoneal (IP), Intra tumoral (IT), Subcutaneous (SC), Intravenous (IV) injections. (A) The average change in tumor size (CM2) from day 0 to day 4 as measured by caliper. (B) Representative images from xenogen imaging are shown on the right. From this data we can conclude that all of the methods of injection effected tumor growth as compared to the untreated mice, and that only the IM treated cohort showed a significantly decreased amount of regression.

FIGS. 24A-24D. Xenograft experiments were run on 6 cell lines, from breast, brain, and prostate. Above are the changes charted in four breast cancer cell lines. (A, B, and D). Graphs of tumor surface area ($cm^2$) as measured by caliper over the indicated days of treatment. (C) The change in HCT-1143 cells is seen after only 24 hours of treatment. In all four cell lines there is a clear reduction in tumor size after treatment.

Figure 25:
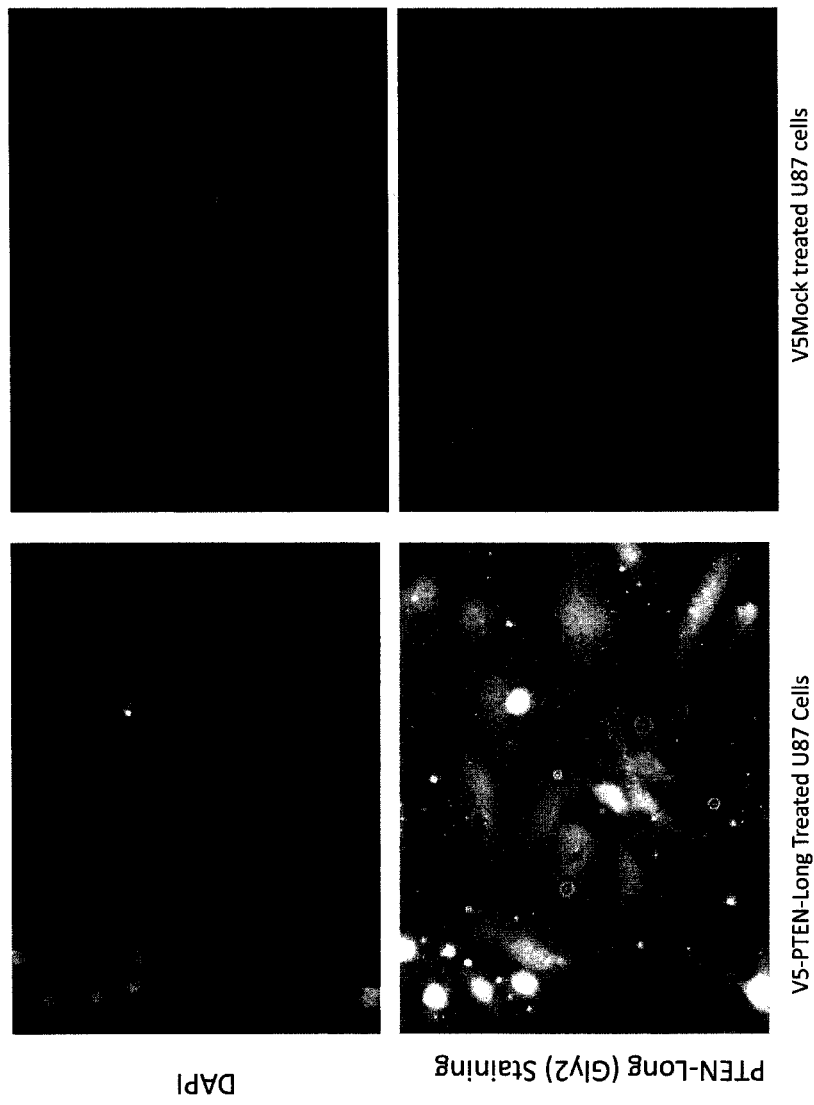

FIG. 25. PTEN-long binds to cells. PTEN-long protein was added to U87 cell media on ice for 10 minutes, fixed and then stained for PTEN-long with the antibody that recognizes it.

FIG. 26. Miles Assay: Induction of vascular permeability is inhibited by PTEN-long. This inhibition can be reversed by pre incubating the purified protein with PTEN antibody (6H2.1). PTEN-long is able to inhibit induction of Vascular permeability by VEGF. This induction could be restored by pre-incubating PTEN-long with antibody raised against PTEN, but not by control IgG.

FIG. 27. The 576 amino acid reading frame (single letter code) (SEQ ID NO:5) of PTEN-Long after mutation of the initiating leucine (L) to methionine (M) to generate a more efficiently translated form. The originally described PTEN 403 amino acid reading frame of PTEN initiates from the underlined codon.

FIG. 28. The MSES version of PTEN-long (SEQ ID NO:6) for expression in bacteria in which the first 21 amino acids have been removed. The C-terminal V5-His epitope tag (SEQ ID NO:7) was fused to the C-terminus (italics). The series of arginines (R) and the last amino acid of the 153 amino acid PTEN-Long leader sequence are underlined.

Figure 29:
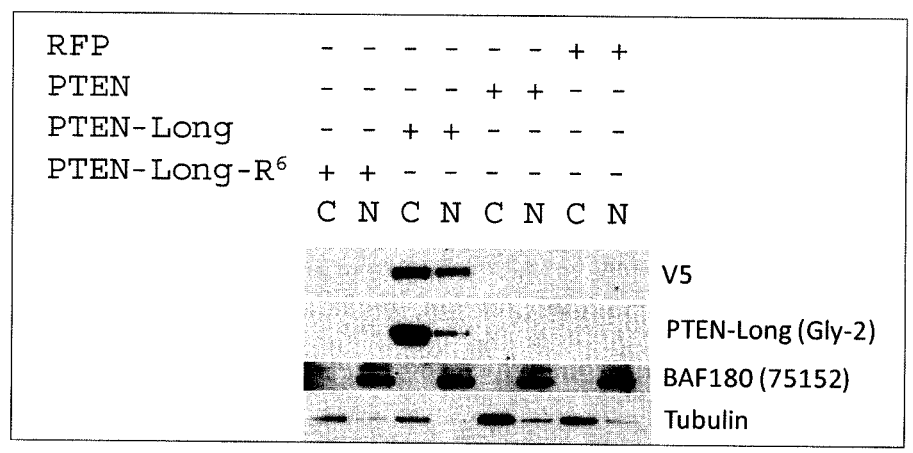

FIG. 29. Western blot of cytoplasmic (C) and nuclear (N) fractions indicates that MSES PTEN-long enters both compartments of the cell. Antibodies for BAF180 and tubulin were used to control for cell fractionation. The V5 epitope was used to measure the entry of all the PTEN constructs. The PTEN-long antibody was used to measure the entry of PTEN long and the $R^6$ deletion.

FIG. 30. Generation of $P_L$-p53. The PTEN long MSES 153 amino acid leader sequence called $P_L$ (underlined) fused to the human p53 393 amino acid sequence (single letter code) (SEQ ID NO:8). The V5 HIS epitope tag (italics) (SEQ ID NO:7) was added to the C-terminus of p53.

Figures 31A, 31B, 31C, 31D:
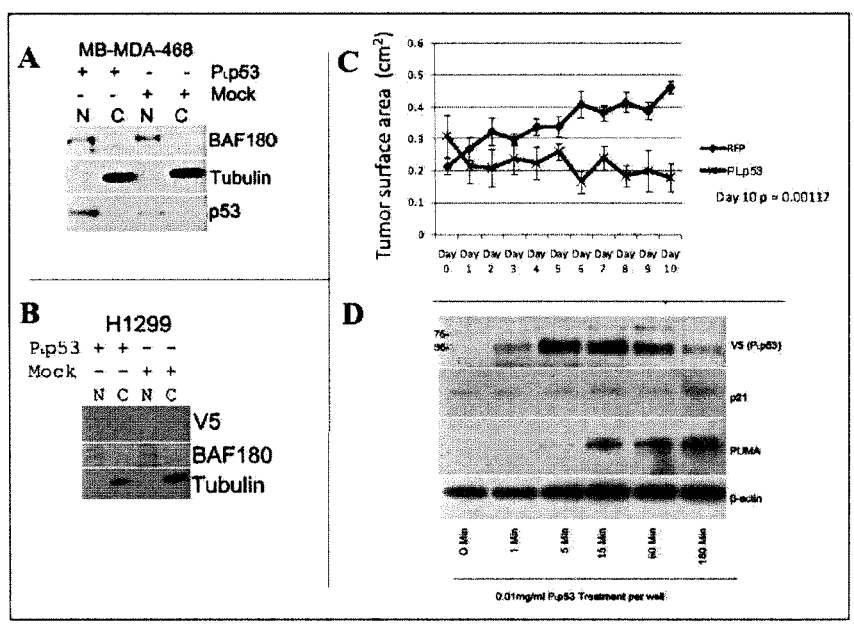

FIG. 31A-31D. $P_L$-p53 enter the nucleus and suppresses tumor growth. Addition of $P_L$-p53 to the media of MDA-MB-468 and H1299 cells (1 mg/ml) leads to uptake into the nucleus (FIGS. 31A and 31B). Nuclear (N) and cytoplasmic (C) separation was monitored with antibodies for the chromatin remodeling factor BAF180 and the cytoplasmic factor tubulin. For MDA-MB468 cells a p53 antibody detected endogenous mutant p53 in the mock treated sample, which was increased in the treated sample. For H1299 cells the V5 epitope fused to $P_L$-p53 was seen only in the treated sample. Treatment of MDA-MB-468 cells with 0.05 mg/day for 10 days led to significant reduction in tumor growth versus the mock treated RFP control (FIG. 31C). Addition of $P_L$-p53 to 1-11299 cell over time shows rapid uptake and induction of PUMA and p21 at subsequent time points (FIG. 32D).

Figure 32:
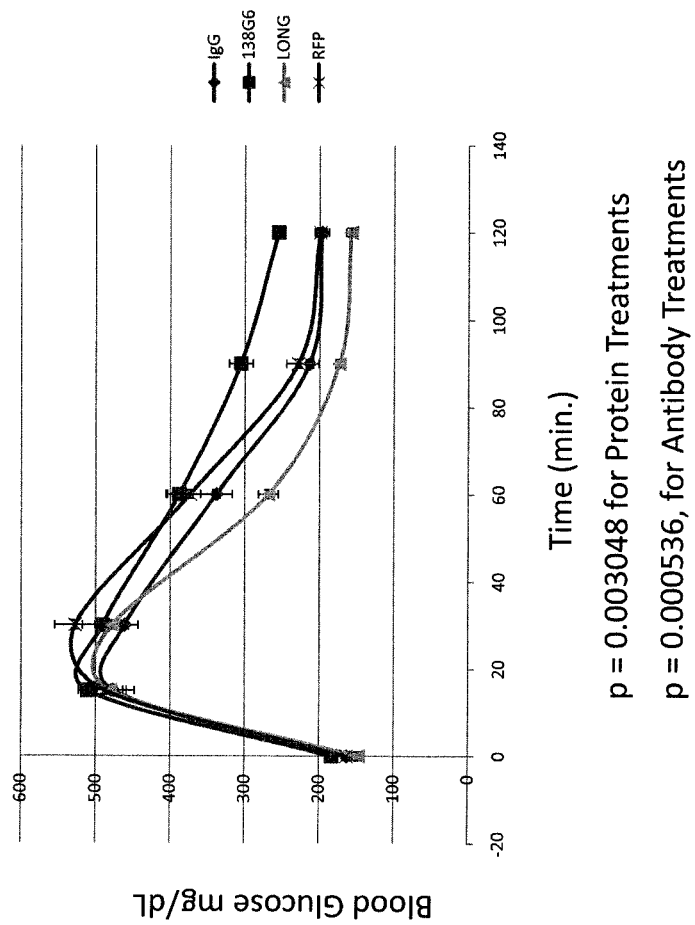

FIG. 32. Glucose tolerance test in mice treat with bacterially expressed MSES PTEN-Long (Long), RFP (red fluorescent protein mock control), IgG control, and anti-PTEN antibody 138G6 that blocks uptake into cells.

DETAILED DESCRIPTION OF THE INVENTION

A composition comprising (i) a peptide comprising consecutive amino acid residues 22-173 of the sequence set forth in SEQ ID NO:1, or a portion of amino acid residues 22-173 of SEQ ID NO:1, for the transport of a cargo molecule across a biological membrane and (ii) the cargo molecule, wherein the cargo molecule is not a peptide comprising amino acid residues having the sequence set forth in SEQ ID NO:4.

In an embodiment the peptide is covalently attached to the cargo molecule. In an embodiment the peptide is covalently attached to the cargo molecule via a disulfide bond. In an embodiment the peptide is non-covalently attached to the cargo molecule.

In an embodiment the cargo molecule is a peptide, a polypeptide, a protein, a nanoparticle, a liposome, a phage, a viral vector, plasmid DNA, a nucleic acid, a peptide nucleic acid, or a morpholino compound. In an embodiment the cargo molecule is a peptide, polypeptide or protein and wherein the peptide for the transport of the cargo molecule is covalently attached to the cargo molecule via a peptide bond. In an embodiment the cargo molecule is a nucleic acid and is a DNA. In an embodiment the cargo molecule is a nucleic acid and is a RNA. In an embodiment the cargo molecule is a nucleic acid and is a siRNA or an antisense oligonucleotide. In an embodiment the cargo molecule is a nucleic acid and encodes a human p53 protein. In an embodiment the cargo molecule is a nucleic acid and encodes a tumor suppressor protein. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1. In an embodiment the cargo molecule is a protein and is a human p53 protein. In an embodiment the cargo molecule is a protein and is a tumor suppressor protein. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1. In an embodiment the cargo molecule is a protein and is an enzyme. In an embodiment the enzyme is a metabolic enzyme. In an embodiment the cargo molecule is a polypeptide or a protein and is an antigen. In an embodiment the cargo molecule is a botulinum toxin or a fragment thereof. In an embodiment the cargo molecule is BCL2 or thioredoxin.

In an embodiment the cargo molecule is a diagnostic agent. In an embodiment the diagnostic agent is a radio-opaque contrast agent, a paramagnetic contrast agent, a superparamagnetic contrast agent, a fluorophore, or a computer tomography contrast agent.

In an embodiment the cargo molecule is a therapeutic agent. In an embodiment the therapeutic agent is a biologically active small molecule. In an embodiment the therapeutic agent is a cytotoxic molecule or a chemotherapeutic agent or a radiotheraputic agent.

In an embodiment the cargo molecule is attached to the peptide for transport via a polymeric linker. In an embodiment the polymeric linker is polyethylene glycol.

In an embodiment the cargo molecule is a nucleic acid. In an embodiment the cargo molecule is a protein and has a molecular weight of up to 160 kDa.

In an embodiment the peptide comprising consecutive amino acid residues having the sequence set forth in SEQ ID NO 1 for the transport of a cargo molecule across a biological membrane is derivatized. In an embodiment the peptide comprises consecutive amino acid residues having the sequence set forth in SEQ ID NO 1.

In an embodiment the composition comprises consecutive amino acid residues having the sequence set forth in SEQ ID NO:8.

A method for delivering a cargo molecule into a cell, comprising contacting the cell with a composition comprising (i) a peptide comprising consecutive amino acid residues 22-173 of the sequence set forth in SEQ ID NO:1, or a portion of the amino acid residues set forth in SEQ ID NO:1, for the transport of the cargo molecule across a biological membrane and (ii) the cargo molecule, wherein the cargo molecule is not a peptide comprising amino acid residues having the sequence set forth in SEQ ID NO 4, under conditions permitting the entry of the cargo molecule into the cell.

In an embodiment the peptide is covalently attached to the cargo molecule. In an embodiment the peptide is covalently attached to the cargo molecule via a peptide bond. In an embodiment the peptide is covalently attached to the cargo molecule via a disulfide bond. In an embodiment the peptide is non-covalently attached to the cargo molecule.

In an embodiment the cargo molecule is a peptide, a polypeptide, a protein, a nanoparticle, a liposome, a phage, a viral vector, plasmid DNA, a nucleic acid, a peptide nucleic acid, or a morpholino compound. In an embodiment the cargo molecule is a peptide, polypeptide or protein and wherein the peptide for the transport of the cargo molecule is covalently attached to the cargo molecule via a peptide bond. In an embodiment the cargo molecule is a nucleic acid and is a DNA. In an embodiment the cargo molecule is a nucleic acid and is a RNA. In an embodiment the cargo molecule is a nucleic acid and is a siRNA or an antisense oligonucleotide. In an embodiment the cargo molecule is a nucleic acid and encodes a human p53 protein. In an embodiment the cargo molecule is a nucleic acid and encodes a tumor suppressor protein. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1. In an embodiment the cargo molecule is a protein and is a human p53 protein. In an embodiment the cargo molecule is a protein and is an enzyme. In an embodiment the enzyme is a metabolic enzyme. In an embodiment the cargo molecule is a protein and is a tumor suppressor protein. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1. In an embodiment the cargo molecule is a polypeptide or a protein and is an antigen. In an embodiment the cargo molecule is a botulinum toxin or a fragment thereof. In an embodiment the cargo molecule is BCL2. In an embodiment the cargo molecule is thioredoxin.

In an embodiment the cargo molecule is a diagnostic agent. In an embodiment the diagnostic agent is a radio-opaque contrast agent, a paramagnetic contrast agent, a superparamagnetic contrast agent, a fluorophore, or a computer tomography contrast agent.

In an embodiment the cargo molecule is a therapeutic agent. In an embodiment the therapeutic agent is a biologically active small molecule. In an embodiment the therapeutic agent is a cytotoxic molecule or a chemotherapeutic agent or a radiotheraputic agent.

In an embodiment the peptide comprises consecutive amino acid residues having the sequence set forth in SEQ ID NO 1. In an embodiment the cell is a tumor cell. In an embodiment the cell is in a human subject.

In an embodiment the composition comprises consecutive amino acid residues having the sequence set forth in SEQ ID NO:8.

A method for treating a tumor in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule, wherein the cargo molecule is not a peptide comprising amino acid residues having the sequence set forth in SEQ ID NO:4 in an amount effective to treat the tumor in the subject.

A composition comprising a peptide comprising amino acid residues 22-173 of SEQ ID NO:1, or a portion of amino acid residues 22-173 of SEQ ID NO:1, conjugated to a cargo molecule, for treating a tumor in a subject, wherein the cargo molecule is not a peptide comprising amino acid residues having the sequence set forth in SEQ ID NO:4 in an amount effective to treat the tumor in the subject.

In an embodiment the cargo molecule is a tumor suppressor protein. In an embodiment the tumor suppressor protein is p53. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1.

In an embodiment the tumor suppressor protein is p53 and the composition comprises consecutive amino acids, the sequence of which is set forth in SEQ ID NO:8.

In an embodiment the peptide comprising amino acid residues 22-173 of SEQ ID NO:1, or portion of amino acid residues 22-173 of SEQ ID NO:1, is covalently attached to the cargo molecule. In an embodiment the peptide comprising amino acid residues 22-173 of SEQ ID NO:1, or portion of amino acid residues 22-173 of SEQ ID NO:1, is covalently attached to the cargo molecule via a peptide bond. In an embodiment the peptide comprising amino acid residues 22-173 of SEQ ID NO:1, or portion of amino acid residues 22-173 of SEQ ID NO:1, is covalently attached to the cargo molecule via a disulfide bond.

In an embodiment the peptide comprising amino acid residues 22-173 of SEQ ID NO:1, or portion of amino acid residues 22-173 of SEQ ID NO:1, is non-covalently attached to the cargo molecule.

A method for treating cancer in a subject comprising administering to the subject an amount of a composition comprising a peptide comprising amino acid residues 22-173 of SEQ ID NO:1, or a portion of amino acid residues 22-173 of SEQ ID NO:1, conjugated to a to a cargo molecule, wherein the cargo molecule is not a peptide comprising amino acid residues having the sequence set forth in SEQ ID NO:4 in an amount effective to treat the cancer in the subject.

A composition comprising a peptide comprising amino acid residues 22-173 of SEQ ID NO:1, or a portion of amino acid residues 22-173 of SEQ ID NO:1, conjugated to a cargo molecule, for treating cancer in a subject, wherein the cargo molecule is not a peptide comprising amino acid residues having the sequence set forth in SEQ ID NO:4 in an amount effective to treat the tumor in the subject.

In an embodiment the cargo molecule is a tumor suppressor protein. In an embodiment the tumor suppressor protein is p53. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1.

In an embodiment the tumor suppressor protein is p53 and the composition comprises consecutive amino acids, the sequence of which is set forth in SEQ ID NO:8.

In an embodiment the peptide comprising amino acid residues 22-173 of SEQ ID NO:1, or portion of amino acid residues 22-173 of SEQ ID NO:1, is covalently attached to the cargo molecule. In an embodiment the peptide comprising amino acid residues 22-173 of SEQ ID NO:1, or portion of amino acid residues 22-173 of SEQ ID NO:1, is covalently attached to the cargo molecule via a peptide bond. In an embodiment the peptide comprising amino acid residues 22-173 of SEQ ID NO:1, or portion of amino acid residues 22-173 of SEQ ID NO:1, is covalently attached to the cargo molecule via a disulfide bond.

In an embodiment the peptide comprising amino acid residues 22-173 of SEQ ID NO:1, or portion of amino acid residues 22-173 of SEQ ID NO:1, is non-covalently attached to the cargo molecule.

A method for treating a metabolic disorder in a subject, wherein the metabolic disorder is characterized by a deficiency in a metabolic enzyme comprising administering to the subject an amount of a composition comprising a peptide comprising amino acid residues 22-173 of SEQ ID NO:1, or portion of amino acid residues 22-173 of SEQ ID NO:1, conjugated to the metabolic enzyme in an amount effective to treat the metabolic disorder in the subject.

A composition comprising a peptide comprising amino acid residues 22-173 of SEQ ID NO:1, or a portion of amino acid residues 22-173 of SEQ ID NO:1, conjugated to a metabolic enzyme for treating a metabolic disorder in a subject, wherein the metabolic disorder is characterized by a deficiency in the metabolic enzyme.

In an embodiment the peptide comprising amino acid residues 22-173 of SEQ ID NO:1, or portion of amino acid residues 22-173 of SEQ ID NO:1, is covalently attached to the metabolic enzyme. In an embodiment the peptide comprising amino acid residues 22-173 of SEQ ID NO: 1, or portion of amino acid residues 22-173 of SEQ ID NO:1, is covalently attached to the metabolic enzyme via a peptide bond. In an embodiment the peptide comprising amino acid residues 22-173 of SEQ ID NO:1, or portion of amino acid residues 22-173 of SEQ ID NO:1, is covalently attached to the metabolic enzyme via a disulfide bond.

In an embodiment the peptide comprising amino acid residues 22-173 of SEQ ID NO:1, or portion of amino acid residues 22-173 of SEQ ID NO:1, is non-covalently attached to the metabolic enzyme.

A method for treating diabetes in a subject comprising administering to the subject an amount of a composition comprising a peptide comprising amino acid residues 22-173 of SEQ ID NO:1, or a portion of amino acid residues 22-173 of SEQ ID NO: 1, conjugated to a cargo molecule in an amount effective to treat the diabetes in the subject.

A composition comprising a peptide comprising amino acid residues 22-173 of SEQ ID NO:1, or a portion of amino acid residues 22-173 of SEQ ID NO:1, conjugated to a cargo molecule for treating diabetes in a subject.

In one embodiment the cargo molecule is a peptide, a polypeptide, a protein, a nanoparticle, a liposome, a phage, a viral vector, plasmid DNA, a nucleic acid, a peptide nucleic acid, or a morpholino compound.

In one embodiment the cargo molecule is a peptide comprising amino acid residues having the sequence set forth in SEQ ID NO:4. In an embodiment the composition comprises consecutive amino acids, the sequence of which is set forth in SEQ ID NO:6.

In an embodiment the cargo molecule is a protein and the protein is a tumor suppressor protein. In an embodiment the tumor suppressor protein is p53. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2. In an embodiment the tumor suppressor protein is RB. In an embodiment the tumor suppressor protein is LKB1. In an embodiment the tumor suppressor protein is p53 and the composition comprises consecutive amino acids, the sequence of which is set forth in SEQ ID NO:8.

In an embodiment the cargo molecule is BCL2. In an embodiment the cargo molecule is thioredoxin.

In an embodiment the peptide comprising amino acid residues 22-173 of SEQ ID NO:1, or portion of amino acid residues 22-173 of SEQ ID NO:1, is covalently attached to the cargo molecule. In an embodiment the peptide comprising amino acid residues 22-173 of SEQ ID NO:1, or portion of amino acid residues 22-173 of SEQ ID NO:1, is covalently attached to the cargo molecule via a peptide bond. In an embodiment the peptide comprising amino acid residues 22-173 of SEQ ID NO:1, or a portion of amino acid residues 22-173 of SEQ ID NO: 1, is covalently attached to the cargo molecule via a disulfide bond.

In an embodiment the peptide comprising amino acid residues 22-173 of SEQ ID NO:1, or a portion of amino acid residues 22-173 of SEQ ID NO:1, is non-covalently attached to the cargo molecule.

A method for treating a cardiovascular disease in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule in an amount effective to treat the cardiovascular disease in the subject.

A composition comprising a peptide comprising amino acid residues 22-173 of SEQ ID NO: 1, or a portion of amino acid residues 22-173 of SEQ ID NO:1, conjugated to a cargo molecule for treating a cardiovascular disease in subject.

In an embodiment the cargo molecule is a peptide, a polypeptide, a protein, a nanoparticle, a liposome, a phage, a viral vector, plasmid DNA, a nucleic acid, a peptide nucleic acid, or a morpholino compound.

In an embodiment the cargo molecule is a peptide comprising amino acid residues having the sequence set forth in SEQ ID NO:4. In an embodiment the composition comprises consecutive amino acids, the sequence of which is set forth in SEQ ID NO:6.

In an embodiment the cargo molecule is a protein and the protein is a tumor suppressor protein. In an embodiment the tumor suppressor protein is p53. In an embodiment the tumor suppressor protein is p16. In an embodiment the tumor suppressor protein is ARF. In an embodiment the tumor suppressor protein is VHL. In an embodiment the tumor suppressor protein is SMAD4. In an embodiment the tumor suppressor protein is ARID1A. In an embodiment the tumor suppressor protein is BAF180. In an embodiment the tumor suppressor protein is BRCA1. In an embodiment the tumor suppressor protein is BRCA2.

In an embodiment the tumor suppressor protein is RB. In an embodiment the tumor suppressor protein is LKB1. In an embodiment the tumor suppressor protein is p53 and the composition comprises consecutive amino acids, the sequence of which is set forth in SEQ ID NO:8.

In an embodiment the cargo molecule is BCL2. In an embodiment the cargo molecule is thioredoxin.

In an embodiment the cardiovascular disease is selected from the group consisting of arteriosclerosis, atherosclerosis, cardiomyopathies, coronary artery disease, peripheral vascular diseases, congestive heart failure, myocardial infarction, and ischemia/re-perfusion injury. In an embodiment the cardiovascular disease is atherosclerosis.

In an embodiment the cardiovascular disease is myocardial infarction. In an embodiment the cardiovascular disease is myocardial infarction and the composition is administered during the myocardial infarction. In an embodiment the composition is administered in an amount effective to prevent cell death.

In an embodiment the peptide comprising amino acid residues 22-173 of SEQ ID NO:1, or a portion of amino acid residues 22-173 of SEQ ID NO:1, is covalently attached to the cargo molecule. In an embodiment the peptide comprising amino acid residues 22-173 of SEQ ID NO:1, or portion of amino acids 22-173 of SEQ ID NO: 1, is covalently attached to the cargo molecule via a peptide bond. In an embodiment the peptide comprising amino acid residues 22-173 of SEQ ID NO:1, or portion of amino acid residues 22-173 of SEQ ID NO: 1, is covalently attached to the cargo molecule via a disulfide bond.

In an embodiment the peptide comprising amino acid residues 22-173 of SEQ ID NO:1, or a portion of amino acid residues 22-173 of SEQ ID NO:1, is non-covalently attached to the cargo molecule.

A peptide "for the transport of a cargo molecule", as used herein, is a peptide which acts as a cell penetrating peptide, i.e. a peptide which mediates transport of a molecule attached thereto (the "cargo molecule") across a biological membrane.

A "cargo molecule" as used herein is a molecule of interest to be transported across a biological membrane, e.g. from the extracellular space to an intracellular space, which is attached covalently or non-covalently to one of the transporting peptides described herein. In the embodiment of the cargo molecule being a peptide, polypeptide or protein, the transporting peptide can be covalently attached through a peptide bond to the cargo molecule so as to form a fusion protein. The PTEN polypeptide as set forth in SEQ ID NO:4 is specifically excluded from the definition of cargo molecule.

As used herein "siRNA" is a double-stranded (ds) RNA, usually about 19-25 nucleotides long, often with 3' overhangs (2 nucleotides) at each end. One method of covalently attaching the siRNA to the peptide for transport of a cargo molecule is via a disulfide bond at the 5' end of an siRNA sense strand.

As used herein, "cardiovascular disease" means a pathological state affecting the normal physiological functioning of a mammalian heart and/or the cardiac blood supply and/or other vascular components including arteriosclerosis, atherosclerosis, cardiomyopathies, coronary artery disease, peripheral vascular diseases, congestive heart failure, myocardial infarction, and ischemia/re-perfusion injury.

A "chemotherapeutic agent", as used herein, is an alkylating agent, anti-metabolite, anthracycline, plant alkaloid, topoisomerase inhibitor, or tyrosine kinase inhibitor used in the art to treat cancer.

A "radiotherapeutic agent", as used herein, is a radioisotope used in the art to treat cancer.

A "small molecule", as used herein, is a low molecular weight organic compound which is not a polymer and which has a molecular weight of less than 1 kDa and more usually less than 800 Da.

In embodiments, the tumor is a cancerous cell. In further embodiments, the cancerous tumor is a tumor of the subject's glial cells, prostate, ovaries, uterus, endometrium, breast, melanocyte, kidney, lung, colon, head, neck, or pancreas.

In an embodiment, the cargo molecule is a tumor suppressor protein. A "tumor suppressor protein" as used herein is a protein, encoded by a tumor-suppressor gene, which has a dampening or repressive effect on the regulation of the cell cycle or promote apoptosis, or sometimes both. Non limiting examples of tumor suppressor proteins include p53. p16, ARF, VHL, SMAD4, ARID1A, BAF180, BRCA1, BRCA2, RB and LKB1.

In an embodiment the cargo molecule is a p53 protein or a p53 encoding nucleic acid (TP53 tumor protein p53, *Homo sapiens*—Entrez Gene GeneID: 7157) or an active fragment thereof, or single nucleotide polymorphism thereof or fragment thereof.

The peptide sequences described herein for transport of cargo molecules are, generically, cell penetrating peptides, although cell penetrating peptides are typically 30 amino acids or less. Delivery of RNA (including siRNA) into cells using a cell penetrating peptide is described in Mathupala et al., *Expert Opin Ther Pat.* 2009 February; 19(2): 137-140, which is hereby incorporated by reference in its entirety. Delivery of vaccines using a cell penetrating peptide is described in Brook et al., Biochim Biophys Acta. 2010 January; 1805(1):25-34, which is hereby incorporated by reference in its entirety. Delivery of delivery of nanoparticles, liposomes, and other nanocarriers is described in Juliano et al. *Wiley Interdiscip Rev Nanomed Nanobiotechnol.* 2009 May; 1(3):324-35, which is hereby incorporated by reference in its entirety. Delivery of chemotherapeutic agents and anti-cancer agents using a cell penetrating peptide is described in Bitler et al., *Recent Pat Anticancer Drug Discov.* 2009 Dec. 2, Epub, which is hereby incorporated by reference in its entirety.

"Treating" a disorder/disease shall mean slowing, stopping or reversing the disorder's progression, and/or ameliorating, lessening, or removing symptoms of the disorder. Thus treating a disorder encompasses reversing the disorder's progression, including up to the point of eliminating the disorder itself.

In an embodiment of the methods described herein the method is used to deliver a prophylactically effective amount of the cargo molecule to a subject. As used herein, a "prophylactically effective" amount of a substance is an amount effective to prevent or to delay the onset of a given pathological condition in a subject to which the substance is administered. In an embodiment of the methods described herein the method is used to deliver a therapeutically effective amount of the cargo molecule to a subject. As used herein, a "therapeutically effective" amount of a substance is an amount effective to treat, ameliorate or lessen a symptom or cause of a given pathological condition in a subject suffering therefrom to which subject the substance is administered.

In one embodiment, the therapeutically or prophylactically effective amount is from about 1 mg of agent/subject to about 1 g of agent/subject per dosing. In another embodiment, the therapeutically or prophylactically effective amount is from about 10 mg of agent/subject to 500 mg of agent/subject. In a further embodiment, the therapeutically or prophylactically effective amount is from about 50 mg of agent/subject to 200 mg of agent/subject. In a further embodiment, the therapeutically or prophylactically effective amount is about 100 mg of agent/subject. In still a further embodiment, the therapeutically or prophylactically effective amount is selected from 50 mg of agent/subject, 100 mg of agent/subject, 150 mg of agent/subject, 200 mg of agent/subject, 250 mg of agent/ subject, 300 mg of agent/subject, 400 mg of agent/subject and 500 mg of agent/subject.

In an embodiment of the methods described herein the composition comprising the peptide and cargo molecule is administered to a subject using any of the various methods and delivery systems known to those skilled in the art. The administering can be, for example, intravenous, oral, nasal, intraperitoneal, via the cerebrospinal fluid, via implant, transmucosal, transdermal, intramuscular, intravascular, intra-arterial, intracoronary, intramyocardial or subcutaneous.

In an embodiment of the methods described herein the composition is administered to the subject by direct introduction into the tumor. In an embodiment of the methods described herein the composition is injected into solid tumor. In an embodiment of the methods described herein the composition is directly introduced into the tumor by a catheter. In an embodiment of the methods described herein the composition is administered to the subject by direct introduction into a blood vessel supplying the tumor. In an embodiment of the methods described herein the composition is injected into the blood vessel supplying the tumor. In an embodiment of the methods described herein the composition is directly introduced by a catheter into the blood vessel supplying the tumor. In an embodiment of the methods described herein the composition is administered to the subject intravenously. In an embodiment of the methods described herein the composition is administered to the subject subcutaneously.

The term PTEN refers to the polypeptide defined by SEQ ID NO:4.

PTEN-long has otherwise sometimes been referred to as PTEN-beta, PTEN-β, PTEN-S.

Injectable drug delivery systems for the compositions described herein, include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as the non limiting examples PLGA and polycaprylactone.

Oral delivery systems for the compositions of the invention include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems for the compositions of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems for the compositions of the invention include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems for the compositions of the invention include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "5'ATR" is the 5' alternately translated region as described in the Experimental section herein below.

In an embodiment, the compositions described herein further comprise a pharmaceutical carrier. As used herein, a "pharmaceutical carrier" is a pharmaceutically acceptable solvent, suspending agent or vehicle, for delivering the instant compositions to the animal or human. The carrier may be liquid, aerosol, gel or solid and is selected with the planned manner of administration in mind.

In an embodiment of the methods described herein the cell is a tumor cell which is a solid tumor cell. "Solid Tumor" as used herein includes cancerous and non-cancerous solid tumors. Cancerous solid tumors include, without limitation, biliary tract cancer; brain cancer, including glioblastomas and medulloblastomas; breast cancer; cervical cancer; choriocarcinoma; colon cancer; endometrial cancer; esophageal cancer; gastric cancer; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilms tumor, but excludes tumors of non-solid tissues such as leukemias and other hematological neoplasms, including acute lymphocytic and myelogenous leukemia; multiple myeloma; AIDS associated leukemias and adult T-cell leukemia lymphoma.

SEQ ID NO:1 of the sequence listing is the leader sequence and signal sequence (residues 1-21) of PTEN-long protein.

SEQ ID NO:2 of the sequence listing is an analogue of the leader sequence and signal sequence (residues 1-21) of PTEN-long protein. In any of the embodiments of the methods and compositions described herein, SEQ ID NO:2 can be used in place of SEQ ID NO:1 where SEQ ID NO:1 is recited.

SEQ ID NO:3 is an epitope on PTEN-long.

SEQ ID NO:4 is the polypeptide of PTEN (i.e. not PTEN-long).

SEQ ID NO:6 is the MSES PTEN-long.

SEQ ID NO:8 is a PTEN-long-p53 fusion protein. In any of the embodiments of the methods and compositions described herein, amino acids 1-153 of SEQ ID NO:8 can be used in place of SEQ ID NO:1 where SEQ ID NO:1 is recited.

In an embodiment of any of the above described methods, the peptide comprising amino acids 22-173 of SEQ ID NO:1, or a portion of SEQ ID NO:1, is a peptide comprising a portion of amino acids 22-173 of SEQ ID NO:1 which retains the ability to transport a cargo molecule across a biological membrane.

Where a range is given in the specification it is understood that the range includes all integers and 0.1 units within that range, and any sub-range thereof. For example, a range of 77 to 90% includes 77.0%, 77.1%, 77.2%, 77.3%, 77.4%, 77.5%, 77.6%, 77.7%, 77.8%, 77.9%, 80.0%, 80.1%, 80.2%, 80.3%, 80.4%, 80.5%, 80.6%, 80.7%, 80.8%, 80.9%, and 90.0%, as well as the range 80% to 81.5% etc.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

First Series of Experiments

The PTEN tumor suppressor is one of the most commonly altered genes in cancer. It functions as a lipid phosphatase of phosphatidylinositol 3,4,5-triphosphate which in turn suppresses oncogenic signaling from phosphatidylinositol 3-kinase (PI3K) and Akt. Inspection of PTEN mRNA revealed that the 5' untranslated region (UTR) is in frame with the open reading frame (ORF) of PTEN for 770 bp. Within this UTR ORF, there is an alternate CUG start codon within a weak Kozak sequence at 513 base pairs upstream of the canonical AUG start codon. While expression of the canonical PTEN ORF generates a protein which migrates at approximately 55 kDa, expression of PTEN cDNA containing the 5'UTR is able to generate a second protein at 70 kDa called PTEN-long. Mutation of the start sites indicated that the 55 kDa PTEN is generated from translation at the canonical start codon while PTEN-long is initiated from the upstream alternate start site. Immunoblotting with different PTEN antibodies demonstrated the endogenous presence of PTEN-long in multiple cells lines. Knockdown and knockout studies in mouse ES cells confirmed that this larger protein was indeed PTEN. The added N-terminal protein sequence encoded a signal peptide and cleavage site, indicating that PTEN-long enters the secretory pathway. PTEN-long preferentially binds the lectin concanavalin A, demonstrating that it is glycosylated. Furthermore, PTEN-long can be purified from conditioned media by affinity purification using both an antibody to PTEN as well as heparan sulfate. PTEN-long is also sensitive to degradation in an in vivo protease protection assay while normal PTEN is not, indicating that PTEN-long is located on the outside of the cell membrane.

Reagents, Cell Lines and Antibodies—

Proteinase K and concanavalin-A were purchased from Sigma (St. Louis, Mo.). Heparin sepharose and HiTrap Heparin HP columns were purchased from Amersham (Piscataway, N.J.). Antibodies to PTEN were purchased from Cell Signaling (Danvers Mass.) and Cascade (Winchester Mass.). Akt antibody was obtained from Cell Signaling (Danvers Mass.) and E cadhein antibody from Upstate Millipore (Bilerica, Ma). A polyclonal affinity purified antibody raised against the epitope PRHQQLLPSLSSFFFSHRLPD (SEQ ID NO:3), found in the novel translation of PTEN, was performed by Zymed Laboratories (South San Francisco, Calif.). Secondary antibodies were purchased from Pierce (Rockford, Ill.). HEK293, ZR-75-1, SKBR-3, MDAMB-361, BT549, and PC3 were obtained from ATCC (Manassas, Va.) and grown according to supplied guidelines.

Figure 1:
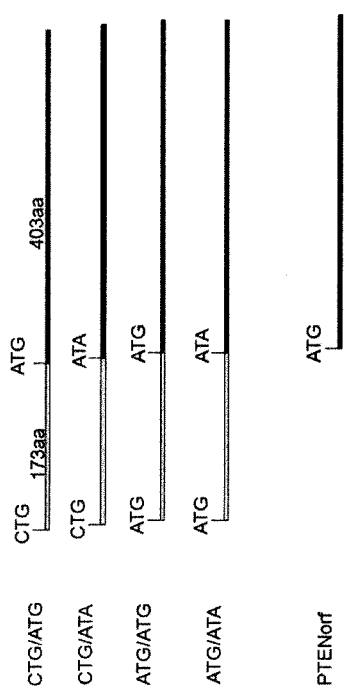
FIG. 1. Diagram of PTEN-long Constructs. Expression constructs showing the combinations created for driving expression of PTEN either from the endogenous start site or the alternate start site. Canonical PTEN is shown in black while the translated region in the UTR is shown in gray.

Plasmids and Constructs— pCEP4-PTEN, encoding the full open reading frame of PTEN and 5'-untranslated region was generated as previously reported by cloning PTEN cDNA (deposited in NCBI as U90351) into the NotI site of pCEP4 (Invitrogen) (Li, Simpson et al. 1998). The 5'UTR was further extended on this plasmid by ligating an adaptor encoding sequence upstream of the original NotI restriction site used for cloning. The adaptor encoded up to 10 base pairs upstream of the first possible alternate CTG start codon located at -513 of the canonical start site. An adaptor in which the putative alternate start site was mutated to ATG was also used to create a second set of expression constructs in which the long form would he efficiently expressed. Furthermore mutagenesis of the canonical start codon to ATA was also performed, yielding in total 4 different constructs (FIG. 1). These 4 variations, as well as the open reading frame of the original PTEN were also subcioned into MSCV (Clontech, Mountainview, CA) retrovirus vector for stable expression via infection.

Protease Protection Assay—

HEK293 cells were collected in ice-cold PBS without trypsin and $5 \times 10^5$ cell aliquots were incubated for 30 minutes with increasing concentrations of Proteinase K, from 0.5 ug/ml to 10 ug/ml. A control with Triton 0.1% was included to verify the ability of Proteinase K to degrade the indicated proteins. The reaction was stopped with 5 mM PMSF. Cells were lysed in 2× Laemmli sample buffer (125 nM Tris pH 6.8, 20% glycerol, 0.05% bromophenol blue, 4% SDS, 10% 2-mercaptoethanol) and immunoblotted for PTEN, Akt and E cadherin.

PTEN Purification from Mouse Livers—

Livers from C57BL6 mice were snap frozen in liquid nitrogen, pulverized, and resuspended in TNN buffer (50 mM Tris pH 7.4, 150 mM NaCl, 0.5% NP-40, 5 mM EDTA, 3% glycerol, 1 mM DTT, 1× Mammalian Protease Cocktail Inhibitors [Sigma]). The suspension was homogenized with a mortar and centrifuged at 40,000 RPM at 4 degrees for 1 hour. Supernatant was filtered successively with 0.45 micron and 0.22 micron filters. A sephacryl 200 size exclusion column (Amersham) was pre-equilibrated with TNN and the sample was applied at a rate of 0.3 ml/hr, followed by buffer. 2 ml fractions were collected and the low molecular weight samples were pooled and applied to a pre-equilibrated HiTrap Hepain HP column (Amersham). The column was washed with three column volumes of TNN and protein was eluted with stepwise 3× column volumes of 0.3M, 0.5M and 1M NaCl TNN solutions. Fractions were collected in 0.5 ml increments and immunoblotted for PTEN.

PTEN Heparin Purification from Media—

HEK293 cells were grown to confluency in 10% FBS DMEM in 15 cm dishes. The cells were incubated overnight with 15 ml of DMEM without EBS. The media from 20 plates was collected and filtered through a 0.45 micron filter. A 1 ml Heparin HP column was equilibrated with DMEM using AktaPrime (AmershamBioscience) using a flow of 4 ml/min at 4° C. Conditioned media was then passed through the column at 1 ml/min. The column was washed with 10 volumes of BC200 (200 mM Nacl, 50 mMT Tris pH7.4, 1 mM EDTA, 0.2% Triton X-100). Proteins were eluted with 5 ml of 1M NaCl at 1 ml/min in 1 ml fractions. The protein concentration of each fraction was determines by OD at 280 nm. Half of each fraction was precipitated with 20% with trichloroacetic acid, washed with cold acetone dried under vacuum. Protein was reconstituted in 20 ul Laemmli lysis buffer and immunoblotted using an antibody to PTEN and PTEN-long.

PTEN Purification from Serum—

Human serum from AB plasma was obtained from Sigma. 1 ml of serum was filtered through a 0.45 micron filter and precleared of antibodies using Protein A/G agarose for 1 hour incubation. Heparin-agarose was incubated with the precleared serum overnight along with a sepharose control and washed the next day with BC150 (150 mM NaCl, 25 mM Tris pH7.4, 1% NP-40, 0.25% Na Deoxycholate, 1 mM EDTA). Proteins were eluted with laemmli sample buffer and immunoblotted for PTEN or secondary only for heavy chain contamination.

Concanavalin A Pulldown—

HEK293 cells were lysed at subconfluency with BC500 (500 mM NaCl, 20 mM Tris pH 7.4, 1% Triton X-100, 1 mM $MnCl_2$, 1 mM $CaCl_2$, 1× Protease Inhibitor Cocktail). The cell lysate was centrifuged and filtered. Pulldowns were performed with 20 microliters of concanavalin A sepharose (Sigma) for 1 hour at 4° C. The resin was washed with BC500 and protein was eluted with Laemmli sample buffer.

Results

PTEN mRNA has an Upstream Alternate Initiation Start Site

Figure 2:
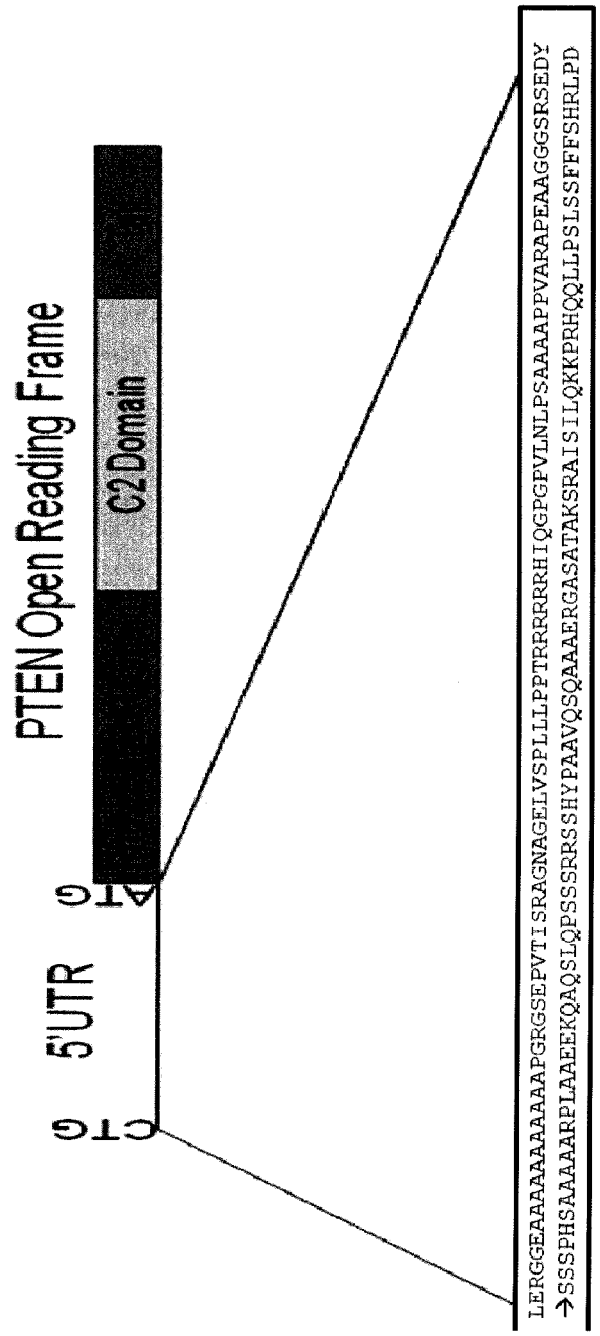
FIG. 2. Diagram of *Homo sapiens* PTEN mRNA. The PTEN mRNA encodes 173 amino acids (SEQ ID NO:9) in frame with and upstream of the canonical ATG start codon shown. Translation begins upstream from the canonical ATG at a CTG at nucleotide −519.

PTEN mRNA deposited into NCBI (Li and Sun 1997; Steck, Pershouse et al. 1997) contains an extensive 5'UTR. Approximately 770 bp of contiguous sequence in the 5'UTR region is in frame with the start codon. No methionines are encoded in this region; however, there are several alternate initiation CUG codons beginning at −519 from the canonical start codon. Translation of this sequence revealed no identifiable domains according to scansite (scansite.mit.edu) and prosite (www.ebi.ac.uk/ppsearch). Translation of this entire region would add 173 amino acids to PTEN increasing its molecular mass to approximately 70 kilodaltons (FIG. 2).

Figure 3:
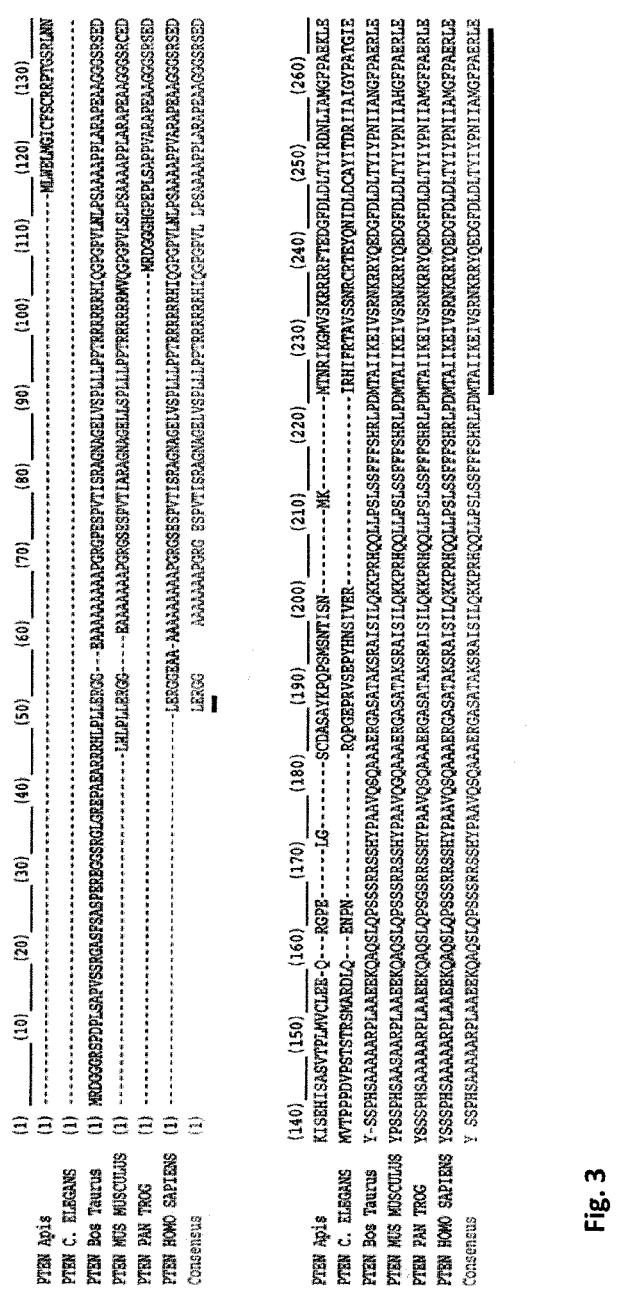

Alignment of other PTEN orthologs revealed that the translated sequence of the *Homo sapiens* UTR can be found in the open reading frames of PTEN from various species. *Pan troglodytes, Bos Taurus, Apis mellifera* and *Caenorhabditis elegans* all contain protein sequence homologous to the translated product of the *Homo sapiens* 5'UTR (FIG. 3). Furthermore, alignment of the *Homo sapiens* 5'UTR and *Mus musculus* PTEN 5'UTR showed extensive nucleotide homology (not shown). The *Mus musculus* 5'UTR was translated in frame with the canonical initiation codon for 522 base pairs and revealed a highly homologous protein sequence when compared to the translation of the *Homo sapiens* 5'UTR (FIG. 3). The homology of the 5'UTR and the actual presence of amino acid sequence derived from *Homo sapiens* 5'UTR in the translated proteins of other species is indicative of the evolutionary importance of this sequence.

PTEN mRNA can Initiate Translation from an Alternate Upstream Site.

Figure 4:
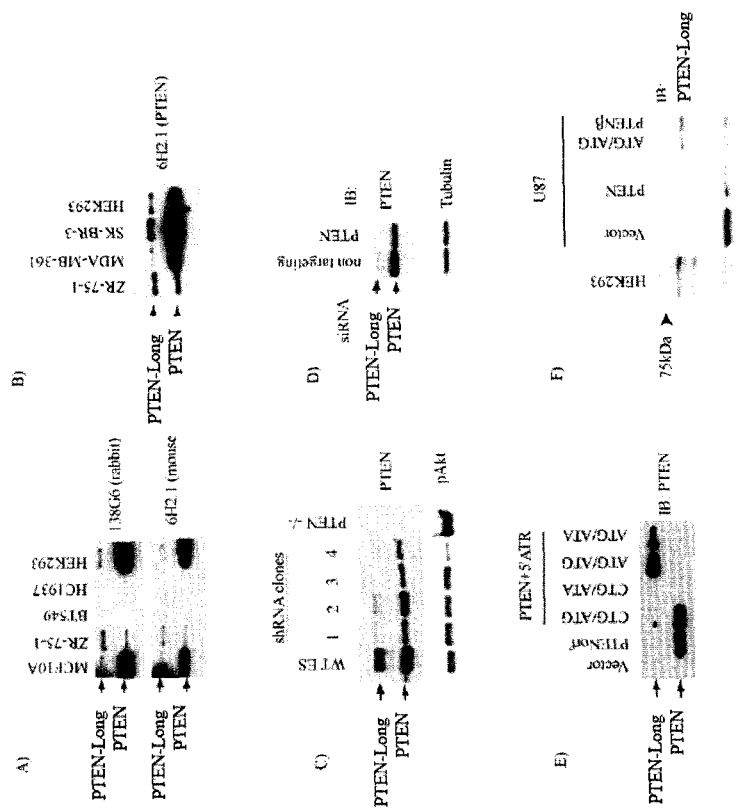
FIG. 4. Evidence for the existence of PTEN-long A) Survey of different cell lines with two different PTEN antibodies. MCF10A and HEK293 are wildtype for PTEN. BT549 and HCC1937 are PTEN null and ZR-75-1 has a mutation in PTEN (L136); B) Further survey of different cell lines with a monoclonal antibody to PTEN which recognizes both PTEN and PTEN-long; C) Wt ES cells express large amount of PTEN-long. PTEN-long is sensitive to stable PTEN shRNA expression in these cells and is completely absent in PTEN knockout cells. pAkt levels for the most part inversely follow the level of PTEN; D) PTEN siRNA causes knockdown of both PTEN and PTEN-long in HEK293 cells. E) Exogneous expression of plasmids in the PTEN null PC3 cell line. PTEN-orf encodes solely the ORF from the start codon AUG (lane 2). Addition of the ATR (ATR=alternately translated region) is able to weakly translate PTEN-long (lane 3). Mutation of the upstream start site to ATG shifted the complement of protein to be completely PTEN-long (lane 5 and 6). Mutation of the ATG start codon to ATA abrogated the 55 kDa band (lane 4 and 6). F) An antibody raised to amino acids encoded by the 5'ATR and used on both a cell lysate from HEK293 as well as in the PTEN null U87 cell line overexpressing either the PTENorf or a plasmid encoding the 5'ATR (ATG/ATG).

Overexpression of the PTEN ORF generated a single protein band at 55 kDa. Inclusion of the 5'UTR resulted in a second larger protein band of approximately 70 kDa. A larger protein band in PTEN immunoblots was also present in a number of cell lines endogenously and was detectable by different monoclonal antibodies (FIG. 4). This larger protein band was also present in mouse wild type ES cells and was absent in PTEN knockout mouse ES cells and decreased in mouse ES clones stably expressing a PTEN shRNA (FIG. 4). Knockdown of human PTEN protein in HEK293 cells using siRNA also caused a knockdown of the 70 kDa protein.

Expression of a plasmid encoding the ORF of PTEN in the PTEN null PC3 cell line resulted in the generation of a 55 kDa protein. When plasmids that also encoded the 5'UTR were overexpressed, a 70 kDa protein was produced. Mutation of the upstream putative initiation codon from CTG to ATG (FIG. 1, "ATG/ATG") predominantly shifted the immunoblot pattern to the 70 kDa form (FIG. 4). The 55 kDa band was also confirmed as originating from the ATG start codon by mutagenesis (FIG. 4 "CTG/ATA").

Thus, the 5' UTR was sufficient to initiate translation of a longer form of PTEN. Accordingly, the 5' UTR was named 5'ATR for Alternately Translated Region and larger protein detected was named "PTEN-long".

An affinity purified polyclonal antibody was generated against amino acids translated from the 5'ATR and it was used to confirm the production of recombinant PTEN-long in overexpression studies as well as the endogenous form in HEK293 cells (FIG. 4). From the whole cell lysate immunoblot of HEK293 cells and overexpression studies in PC3 cells, there appeared to be multiple forms of PTEN-long, indicating either potential post-translational modifications, undocumented splice forms or even alternate initiation codons in the 5'ATR.

PTEN-Long Encodes a N-Terminal Signal Peptide

The N-terminal sequence of PTEN-long contains a long stretch of alanines which could be indicative of either a transmembrane sequence or a signal peptide. Analysis of the translated sequence using SignalIP 3.0 predicted with a high degree of probability (>95%) that the sequence contains a signal peptide (FIG. 5). A signal peptide is characteristically comprised of basic amino acids followed by a hydrophobic stretch. The putative hydphobobic transmembrane helix is broken by a proline and followed by a somewhat polar sequence. The sequence was also predicted to be cleaved, indicating that the protein should be released into the lumen of the ER.

One of the hallmarks of secreted and extracellular proteins is the addition of complex sugar moieties in the golgi apparatus, a process known as glycosylation. Sugars can be added to asparagines at the consensus sequence N-X-S/T (X cannot be proline) via N-glycosylation (Gupta and Brunak 2002); the hydroxyl groups of serines, threonines and tyrosines can also be the target of what has been termed O-glycosylation (Julenius, Molgaard et al. 2005). PTEN has multiple O-glycosylation sites, but only one N-glycosylation site. Lectin concanavalin-A, which binds sugar moieties, was used in a pull-down assay to determine whether a portion of the PTEN complement in HEK293 cells was glycosylated. A mixture of PTEN that was approximately 50% PTEN-long (FIG. 6) was purified from these cells. This shows that PTEN-long is glycosylated and that either the cytoplasmic 55 kDa form of PTEN is glycosylated or that PTEN-long is cleaved extracellularly.

PTEN-Long Binds Heparan and is Found on the Cell Surface

PTEN bound a number of proteoglycans, such as syndecans and glypicans, which are found attached to the outer leaflet of the membrane. These proteoglycans are two of the most heparanated extracellular molecules (Blero, Zhang et al. 2005). PTEN has previously been shown to have high affinity for highly negatively charged species, a property of PTEN which leads to its preference of the highly anionic PIP3 (Das, Dixon et al. 2003). As heparan is one of the most negatively charged biological molecules, it was possible that heparan could mediate the binding of PTEN to the extracellular matrix. Using protein extracts from mouse livers, it was discovered that PTEN bound heparan with high affinity. Furthermore, continuous elution of PTEN from a heparin agarose column using 1M NaCl, also eluted PTEN-long (FIG. 7).

PTEN-long stuck to the external surface of a cell membrane, should be sensitive to protease degradation. In the protease protection assay, live cells are incubated with a protease and only extracellular proteins are degraded as the lipid membrane is impermeable to the protease and serves to protect all intracellular proteins. HEK293 cells were removed from adherent culture by gentle agitation with PBS and suspended with increasing concentrations of Proteinase K. The reaction was stopped with PMSF and cells were lysed with laemlli buffer. PTEN-long displayed sensitivity to treatment with Proteinase K along with E-cadherin, which is a known extracellular protein (FIG. 8). PTEN on the other hand showed modest protease sensitivity, which indicates that some portion of the 55 kDa species is also extracellular (as it is glycosylated) or some cellular lysis occurred during the assay that exposed cytoplasmic PTEN to Proteinase K. A control with membrane permeabilizing triton was included to prove that PTEN could be degraded if exposed to Proteinase K. It remains to be seen whether this is PTEN proper or a cleaved form of PTEN-long which migrates at 55 kDa and retains the C-terminal epitope of the PTEN antibody. This data indicates that PTEN-long is on the cell surface.

Soluble PTEN-Long is Secreted into Media.

The presence of PTEN-long on the cell surface does not exclude the possibility that a portion of the protein is soluble and released into the cellular environment. Heparin sepharose was used to affinity purify PTEN-long from serum free media conditioned on HEK293 cells. Elution of the column revealed the presence of PTEN in the media migrating at a molecular weight of 50 kDa (FIG. 9). An immunoblot with the PTEN-long specific antibody revealed the same 50 kDa species, indicating that this protein retains sequence translated from the alternate start site and sequence from the C-terminal epitope of the PTEN monoclonal antibody. This strongly implies that the portion of PTEN observed to be 55 kDa is in fact cleaved translation product originating from the upstream start codon.

Secretion of PTEN into the media was further confirmed by overexpressing PTEN-long in HEK293 cells transfected with the ATG/ATG construct. These cells were used to produce serum free conditioned media overnight and the PTEN monoclonal antibody 6H2.1 was used to immunoprecipitate PTEN from 1 ml of media. The larger PTEN band was successfully immunoprecipitated from media along with the lower 55 kDa band. Because the protein was overexpressed, proper processing of the protein probably did not occur which resulted in the secretion of the full size 70 kDa PTEN.

PTEN is Found in Human Serum.

One of the best sources of physiological secreted material is serum. Heparin sepharose was used to affinity purify PTEN from human serum. Human serum was spun down and filtered to remove particulate matter. It was then diluted 1:5 in BC150 and precleared extensively with protein A/G to remove IgG. The serum was batch incubated with a small amount of heparin sepharose. The heparin sepharose was eluted with laemmli buffer and the eluate was blotted for PTEN and for just secondary antibody alone to rule out heavy chain contamination. PTEN and PTEN-long were both found in human serum (FIG. 10).

Anti-Angiogenic Activity of PTEN-Long

The anti-angiogenic role of PTEN-long is shown by the following: (1) PTEN-long is normally weakly expressed in the developing retina of the mouse but high level expression is seen in blood vessels undergoing involution/cell death during neonatal development (FIG. 11): (2) PTEN-long is found in apoptosing blood vessels in tumors. Furthermore, epithelial cells treated with PTEN-long, partially purified from transfected cells, inhibited cellular migration and induced apoptosis. (FIG. 12). Purified PTEN-long can also induce cell death associated with activation of apoptosis in U87, HUVEC endothelial cells, or 293 cells in culture, as measure by caspase-3 cleavage.

In Vivo Anti-Tumor and Anti-Angiogenic Activity of PTEN-Long

FIG. 13 shows treatment of Mice with PTEN-long (A) Mice (n=5) were injected with the glioblastoma cell line U87 to form xenografts at 2 sites (left and right) in mammary fat pads. After tumor engraftment one tumor was directly injected with PTEN-long and the contralateral tumor was not injected (w/PTEN-long). A control set of 5 mice also injected (Empty Vector) with a preparation of mock purified protein derived from cells transfected with empty vector. Again, the contralateral tumor was not injected (w/Empty Vector). Mice were treated on days 1-11 and days 13-14. Largest diameter (cm) was measured with calipers on indicated days. Mice were sacrificed when tumor volume reached ≥1 cm. (B) Protein was prepared by transfection of PTEN-long expression vector into 293 cells and partially purified using V5 affinity resin followed by elution with V5 peptide. FIG. 14 Shows the surviving fraction of mice (in days) treated with control injections of PTEN-long for 14 days.

Retinal Staining

Staining for PTEN-long and Blood vessels in the p7 murine retina revealed that PTEN-long selectively stained hyaloid vessels which are beginning to regress at this point in murine retinal vascular development. The antibody to PTEN-long was directed against the epitope: N-PRHQQLLPSLSSFFF-SHRLPD-C (SEQ ID NO:3). Vessel staining was with BS1-lectin.

Purification

In one method for purification of PTEN-long 293 cells were transfected with ATG/ATG PTEN-long and cell lysate was passed over a Ni+ affinity column. PTEN-long was consistently purified using a Ni+ column on the AKTA Purifier using imidazole elution buffer.

Tumor Regression

Xenografts of U87 cells transfected prior to injection with either PTEN (orf 403 amino acid) or PTEN-long. At 7 days post injection there is a reduction in the mammary blood vessels in the PTEN-long over-expressing cohort as compared to the PTEN over-expressing cohort (n=4 of 4). This suggests that PTEN-long can affect the tumor environment.

Transmembrane Delivery by PTEN-Long Leader Sequence

Figure 18:
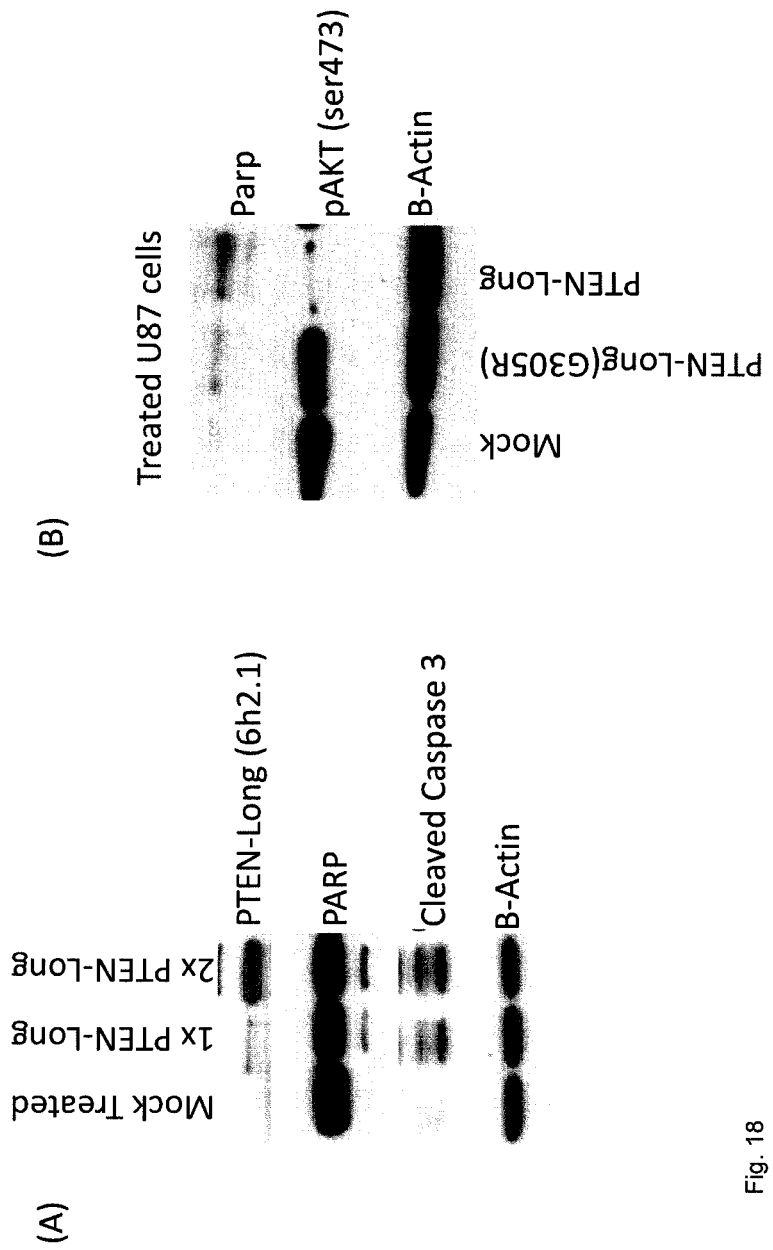
Figure 21:
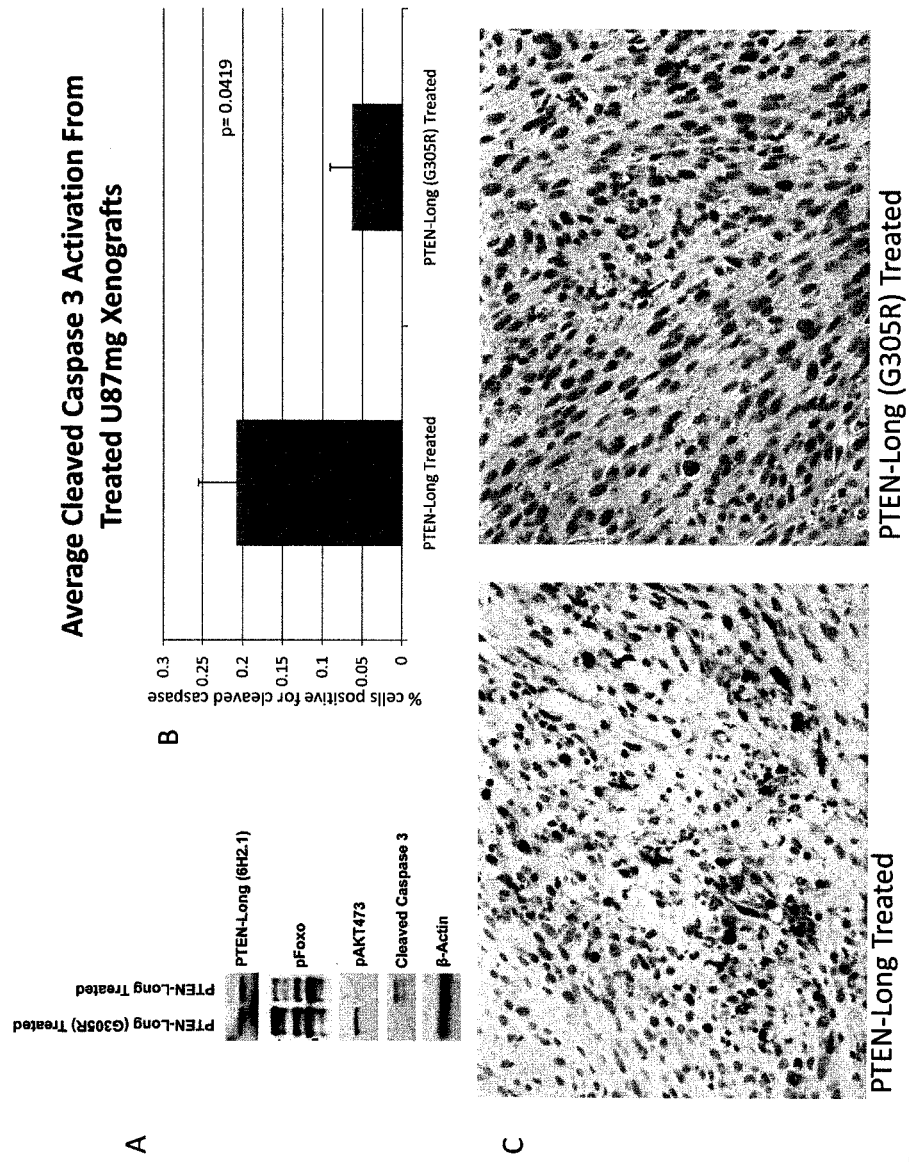

FIGS. 18 and 21 show the ability of PTEN-Long, but not PTEN, to reduce intracellular AKT phosphorylation when it is applied to intact cells.

EXAMPLES

A cargo molecule peptide is covalently attached via a peptide bond to a second peptide which comprises consecutive amino acid residues having the sequence set forth in residues 22-173 of SEQ ID NO 1. On contacting a cell membrane with this composition, the cargo molecule peptide is transported across the cell membrane and delivered into the cell.

A cargo molecule protein is covalently attached via a peptide bond to a peptide which comprises consecutive amino acid residues having the sequence set forth in residues 22-173 of SEQ ID NO 1. On contacting a cell membrane with this composition, the cargo molecule protein is transported across the cell membrane and delivered into the cell. The cargo molecule protein can be human p53, or an active fragment or active variant thereof.

A cargo molecule peptide is covalently attached to a nucleic acid which comprises consecutive amino acid residues having the sequence set forth in residues 22-173 of SEQ ID NO 1. On contacting a cell membrane with this composition, the cargo molecule nucleic acid is transported across the cell membrane and delivered into the cell. The nucleic acid can be covalently attached to the peptide via a disulfide bond. The nucleic acid can be an siRNA.

Discussion

A second larger protein band in PTEN immunoblots from cell lysates and tissue was regularly observed. Evidence confirming that the larger band is PTEN includes: the larger protein bands were detected by different PTEN monoclonal antibodies; the larger protein is absent when cells are treated with siRNA against PTEN or the PTEN locus is knocked out in mice. The 5'UTR of PTEN was observed to be in frame for more than 700 base pairs with the classic start codon of PTEN. Furthermore, there is a CUG codon 522 base pairs upstream of PTEN, which, if translated, could account for the size of the larger protein band in PTEN immunoblots. Though it is not associated with a strong Kozak sequence, it does retain the −1 cytosine and +1 guanosine sequence. When translated and added to the PTEN ORF, a protein of approximately 70 kDa should be created, which is the molecular mass of the larger PTEN band that has been observed.

The translation of this sequence already existed in a number of PTEN orthologs within their actual coding sequence. The mouse 5'UTR was also inspected because a similar band in mouse tissue lysates had been observed. The mouse 5'UTR nucleotide sequence was highly homologous to the *Homo sapiens* 5'UTR and similarly in frame with the start codon. Two potential alternate start codons exist at −522 and −516 and translation of this sequence from those sites reveals amino acid sequence 90%+ homologous to the *Homo sapiens* sequence. The conservation of this putative protein is remarkable and demonstrated an evolutionary importance to this sequence. In order to better describe this sequence, it was renamed the 5'ATR or alternately translated region of PTEN to describe its potential for translation.

A plasmid was constructed in which the open reading frame of PTEN was cloned together with the 5'ATR and the expression of this recombinant PTEN was compared to the canonical 403 amino acid-producing open reading frame alone. The inclusion of the 5'ATR generated a second, higher PTEN protein band which migrated at approximately 70 kDa as compared to expression plasmids containing just the canonical ORF of PTEN, which created a single band migrating at 55 kDa. The larger protein accounted for only a minor portion of the total protein translated; however, mutation of the putative start site to ATG shifted the protein ratio to predominantly the larger form.

The conservation of protein sequence from the 5'ATR indicated that it was more than an artifact of evolution. The N-terminus contained a stretch of aliphatic amino acids which were predicted to be a transmembrane sequence. Use of Prosite and Signal 3.0IP predicted that the N-terminus of PTEN-long was a signal peptide with a protease cleavage site directly following it.

An in vivo protease protection assay was used to test if PTEN-long was located on the extracellular surface of the cells. PTEN-long showed progressive degradation with increasing amounts of extracellular protease, while PTEN did not, indicating that at least some of PTEN-long is extracelluar and at least in part attached to outer leaflet of the cell membrane. This is a most intriguing result given the implication of an active lipid phosphatase on the outer leaflet of the cell membrane. Two families of outer membrane bound proteoglycans, glypicans and syndecans, were previously identified in a PTEN protein complex.

The presence of PTEN on the cell surface does not exclude the possibility of a soluble secreted PTEN. Syndecans and glypicans are two of the most heavily heparanated proteoglycans. Heparan is a highly negatively charged glycosaminoglycan and PTEN has been shown to have an affinity for anions, in part explaining the choice of the highly negatively charged PIP3 as its substrate. Optimization experiments of PTEN purification from mouse liver revealed that both PTEN and PTEN-long could be purified using a heparin sepharose column. Furthermore, a protein of approximately 50 kDa was purified, from serum free media conditioned on HEK293 cells, using a heparin sepharose column. The purified protein was recognized by a monoclonal antibody specific against PTEN and a polyclonal antibody against unique amino acid residues present in PTEN-long. Previously the PTEN-long antibody only recognized a protein band around 70 kDa. The observation that both antibodies could recognize the one band indicates that proteolytic processing is probably occurring and that the protein observed by immunoblot is a fragment of PTEN which retained the epitopes of both antibodies. Both PTEN and PTEN-long could also be purified from human serum using heparin affinity purification.

A body of literature over the past 10 years has accumulated assuming the sequence of PTEN. Here proof for the existence of a novel form of PTEN which is translated from an alternate site and is secreted to both the outer leaflet as well as extracellular spaces.

The in vivo results show that PTEN-long is a novel antitumor compound that is normally present in human serum and which has anti-angiogenic and pro-apoptotic properties.

Second Series of Experiments
Generation of MSES PTEN-Long.

For the purpose of purification in *e. coli*, the PTEN-Long open reading frame was altered to delete the first 21 amino acids to remove the eukaryotic signal peptide sequence, which was termed the MSES version based upon its first four amino acids (FIG. 28). This protein, which has 153 amino acids of the alternatively translated region unique to PTEN-Long and the 403 amino acids shared between PTEN-Long and PTEN, was induced in *e. coli* using an inducible expression vector with IPTG and purified from extracts using nickel and heparin affinity columns. For the purpose of examining the importance of the six arginine repeat for cell entry, this sequence was deleted in frame ($R^6$) and the protein was purified as above.

MSES PTEN-Long Enters Cells.

Purified MSES PTEN-long wild type or $R^6$ mutant protein was added to media of MDA-MB-468 human cells grown in culture at a concentration of 1 microgram/ml. Under parallel identical conditions, cells were also treated with the original 403 amino acid PTEN lacking the alternatively translated region or a mock treatment prepared from cells expressing only the RFP protein. Cells were incubated at 37 degrees for 30 minutes before isolation of cells for cell fractionation. We isolated cytoplasmic and nuclear fractions. Effectiveness of fractionation was measured by western blotting with tubulin and BAF180 to control for cytoplasmic and nuclear fractions, respectively. Only wild-type PTEN-Long entered the cell and was present in the cytoplasm and nucleus. Importantly neither PTEN nor PTEN-Long deleted for $R^6$ was able to enter the cell. These data indicate that the $R^6$ sequence is required for efficient cell entry and that the initial 21 amino acids is not.

Generation of PTEN-Long-p53 Fusion Protein.

The above studies suggested that the first 153 amino acids of the construct in FIG. 2 could be used to deliver another protein sequence into a cell. To ask this question the initial 153 amino acids of the MSES PTEN-Long construct, which is called $P_L$ for Pten-Long Leader, was fused to the 393 amino acids of human p53 to generate a $P_L$-p53 fusion protein (FIG. 30). A V5-His epitope tag was fused to the C-terminus to use for purposes of purification and detection.

$P_L$-p53 Enters Cells, Activates Gene Expression and Suppresses Tumor Growth.

$P_L$-p53 fusion protein was induced in *e. coli* using IPTG and purified from bacterial lysates using nickel and heparin affinity columns. $P_L$-p53 protein was incubated with MDA-MB-468 or H1299 human cancer cells for 1 hr before collecting cells for fractionation to determine if the fusion protein could enter cells. Increased p53 could be detected in the nucleus of treated but not mock treated H1299 cells and MDA-MB-468 cells and was associated with an increase in the expression of PUMA and p21, both targets of the p53 transcription factor (FIG. 31). Daily treatment of MDA-MB-468 xenografts led to a reduction in tumor volume over a 10 day period but the mock treated control prepared from *e. coli* expressing RFP (red fluorescent protein) did not.

Glucose Tolerance Test in Mice Treat with Bacterially Expressed MSES PTEN-Long

Mice were treated with bacterially expressed MSES PTEN-long (Long), RFP (red fluorescent protein mock control). IgG control, and anit-PTEN antibody 138G6 that blocks uptake into cells. PTEN-long reduced glucose level versus other treatments, while the anti-PTEN antibody 138G6 increased glucose relative to IgG control (FIG. 32). This data demonstrate that PTEN-long can reduce blood glucose. Mice were injected IP before treating with glucose.

REFERENCES

Acland, P., M. Dixon, et al. (1990). "Subcellular fate of the int-2 oncoprotein is determined by choice of initiation codon." Nature 343(6259): 662-5.

Alberts, B. (2002). Molecular biology of the cell. New York, Garland Science.

Baker, S. J. (2007). "PTEN enters the nuclear age." Cell 128(1): 25-8.

Blero, D., J. Zhang, et al. (2005). "Phosphatidylinositol 3,4,5-trisphosphate modulation in SHIP2-deficient mouse embryonic fibroblasts." Febs J 272(10): 2512-22.

Blobel, G., P. Walter, et al. (1979). "Translocation of proteins across membranes: the signal hypothesis and beyond." Symp Soc Exp Biol 33: 9-36.

Bonneau, D. and M. Longy (2000). "Mutations of the human PTEN gene." Hum Mutat 16(2): 109-22.

Di Cristofano, A., B. Pesce, et al. (1998). "Pten is essential for embryonic development and tumour suppression." Nat Genet. 19(4): 348-55.

Eng, C. (2003). "PTEN: one gene, many syndromes." Hum Mutat 22(3): 183-98.

Florkiewicz, R. Z. and A. Sommer (1989). "Human basic fibroblast growth factor gene encodes four polypeptides: three initiate translation from non-AUG codons." Proc Natl Acad Sci USA 86(11): 3978-81.

Fraser, M. M., X. Zhu, et al. (2004). "Pten loss causes hypertrophy and increased proliferation of astrocytes in vivo." Cancer Res 64(21): 7773-9.

Gupta, R. and S. Brunak (2002). "Prediction of glycosylation across the human proteome and the correlation to protein function." Pac Symp Biocomput: 310-22 Hann, S. R. (1994). "Regulation and function of non-AUG-initiated proto-oncogenes." Biochimie 76(9): 880-6.

Hann, S. R., M. Dixit, et al. (1994). "The alternatively initiated c-Myc proteins differentially regulate transcription through a noncanonical DNA-binding site." Genes Dev 8(20): 2441-52.

Hann, S. R. and R. N. Eisenman (1984). "Proteins encoded by the human c-myc oncogene: differential expression in neoplastic cells." Mol Cell Biol 4(11): 2486-97.

Hann, S. R., M. W. King, et al. (1988). "A non-AUG translational initiation in c-myc exon 1 generates an N-terminally distinct protein whose synthesis is disrupted in Burkitt's lymphomas." Cell 52(2): 185-95.

Hann, S. R., K. Sloan-Brown, et al. (1992). "Translational activation of the non-AUG-initiated c-myc 1 protein at high cell densities due to methionine deprivation." Genes Dev 6(7): 1229-40.

Hershey, J. W. (1991). "Translational control in mammalian cells." Annu Rev Biochem 60: 717-55.

Julenius, K., A. Molgaard, et al. (2005). "Prediction, conservation analysis, and structural characterization of mammalian mucin-type O-glycosylation sites." Glycobiology 15(2): 153-64.

Kiefer, P., P. Acland, et al. (1994). "Competition between nuclear localization and secretory signals determines the subcellular fate of a single CUG-initiated form of FGF3." Embo 13(17): 4126-36.

Kozak, M. (1989). "Context effects and inefficient initiation at non-AUG codons in eucaryotic cell-free translation systems." Mol Cell Biol 9(11): 5073-80.

Kozak, M. (1990). "Downstream secondary structure facilitates recognition of initiator codons by eukaryotic ribosomes." Proc Natl Acad Sci USA 87(21): 8301-5.

Kozak, M. (1991). "An analysis of vertebrate mRNA sequences: intimations of translational control." J Cell Biol 115(4): 887-903.

Kwabi-Addo, B., D. Giri, et al. (2001). "Haploinsufficiency of the Pten tumor suppressor gene promotes prostate cancer progression." Proc Natl Acad Sci USA 98(20): 11563-8.

Lee, J. O., H. Yang, et al. (1999). "Crystal structure of the PTEN tumor suppressor: implications for its phosphoinositide phosphatase activity and membrane association." Cell 99(3): 323-34.

Li, J., L. Simpson, et al. (1998). "The PTEN/MMAC1 tumor suppressor induces cell death that is rescued by the AKT/protein kinase B oncogene." Cancer Res 58(24): 5667-72.

Maehama, T. and J. E. Dixon (1998). "The tumor suppressor, PTEN/MMAC1, dephosphorylates the lipid second messenger, phosphatidylinositol 3,4,5-trisphosphate." J Biol Chem 273(22): 13375-8.

Petrocelli, T. and J. M. Slingerland (2001). "PTEN deficiency: a role in mammary carcinogenesis." Breast Cancer Res 3(6): 356-60.

Prats, H., M. Kaghad, et al. (1989). "High molecular mass forms of basic fibroblast growth factor are initiated by alternative CUG codons." Proc Natl Acad Sci USA 86(6): 1836-40.

Sulis, M. L. and R. Parsons (2003). "PTEN: from pathology to biology." Trends Cell Biol 13(9): 478-83.

Taira, M., T. Iizasa, et al. (1990). "A human testis-specific mRNA for phosphoribosylpyrophosphate synthetase that initiates from a non-AUG codon." J Biol Chem 265(27): 16491-7.

Torres, J. and R. Pulido (2001). "The tumor suppressor PTEN is phosphorylated by the protein kinase CK2 at its C terminus. Implications for PTEN stability to proteasome-mediated degradation." J Biol Chem 276(2): 993-8.

Vazquez, F., S. R. Grossman, et al. (2001). "Phosphorylation of the PTEN tail acts as an inhibitory switch by preventing its recruitment into a protein complex." J Biol Chem 276 (52): 48627-30.

Vazquez, F., S. Ramaswamy, et al. (2000). "Phosphorylation of the PTEN tail regulates protein stability and function." Mol Cell Biol 20(14): 5010-8.

Wang, X., L. C. Trotman, et al. (2007). "NEDD4-1 is a proto-oncogenic ubiquitin ligase for PTEN." Cell 128(1): 129-39.

Xiao, J. H., 1. Davidson, et al. (1991). "Cloning, expression, and transcriptional properties of the human enhancer factor TEF-1." Cell 65(4): 551-68.

You, M. J. D. H. Castrillon, et al. (2002). "Genetic analysis of Pten and Ink4a/Arf interactions in the suppression of tumorigenesis in mice." Proc Natl Acad Sci USA 99(3): 1455-60

What is claimed is:

1. A composition comprising (i) a peptide comprising consecutive amino acid residues 22-173 of the sequence set forth in SEQ ID NO:1, or a portion of amino acid residues 22-173 of SEQ ID NO:1, for the transport of a cargo molecule across a biological membrane and (ii) the cargo molecule, wherein the cargo molecule is not a peptide comprising amino acid residues having the sequence set forth in SEQ ID NO:4, wherein the cargo molecule is attached to the peptide for transport via a polymeric linker.

2. A method for delivering a cargo molecule into a cell, comprising contacting the cell with a composition comprising (i) a peptide comprising consecutive amino acid residues 22-173 of the sequence set forth in SEQ ID NO:1, or a portion of the amino acid residues set forth in SEQ ID NO:1, for the transport of the cargo molecule across a biological membrane and (ii) the cargo molecule, wherein the cargo molecule is not a peptide comprising amino acid residues having the sequence set forth in SEQ ID NO:4, under conditions permitting the entry of the cargo molecule into the cell, wherein the cargo molecule is a nucleic acid and encodes a human p53 protein.

3. A method for delivering a cargo molecule into a cell, comprising contacting the cell with a composition comprising (i) a peptide comprising consecutive amino acid residues 22-173 of the sequence set forth in SEQ ID NO:1, or a portion of the amino acid residues set forth in SEQ ID NO:1, for the transport of the cargo molecule across a biological membrane and (ii) the cargo molecule, wherein the cargo molecule is not a peptide comprising amino acid residues having the sequence set forth in SEQ ID NO:4, under conditions permitting the entry of the cargo molecule into the cell, wherein the cargo molecule is a human p53 protein.

4. A method for treating cancer in a subject comprising administering to the subject an amount of a composition comprising a peptide comprising amino acid residues 22-173 of SEQ ID NO:1, or a portion of amino acid residues 22-173 of SEQ ID NO:1, conjugated to a to a cargo molecule, wherein the cargo molecule is not a peptide comprising amino acid residues having the sequence set forth in SEQ ID NO:4 in an amount effective to treat the cancer in the subject, wherein the cargo molecule is a tumor suppressor protein.

5. A method for treating a metabolic disorder, wherein the metabolic disorder is characterized by a deficiency in a metabolic enzyme comprising administering to the subject an amount of a composition comprising a peptide comprising amino acid residues 22-173 of SEQ ID NO:1, or portion of amino acid residues 22-173 of SEQ ID NO:1, conjugated to the metabolic enzyme in an amount effective to treat the metabolic disorder in the subject.

6. A method for treating diabetes in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule in an amount effective to treat the diabetes in the subject.

7. A method for treating a cardiovascular disease in a subject comprising administering to the subject an amount of a composition comprising a peptide comprising amino acid residues 22-173 of SEQ ID NO:1, or a portion of amino acid residues 22-173 of SEQ ID NO:1, conjugated to a cargo molecule in an amount effective to treat the cardiovascular disease in the subject.

* * * * *